United States Patent [19]

Martin et al.

[11] Patent Number: 5,041,663

[45] Date of Patent: Aug. 20, 1991

[54] NOVEL OXIME ETHERS, THE PREPARATION THEREOF, COMPOSITIONS CONTAINING THEM AND THE USE THEREOF

[75] Inventors: Henry Martin, Basel; Urs Fricker, Gelterkinden, both of Switzerland

[73] Assignee: Ciba-Geigy Corporation, Ardsley, N.Y.

[21] Appl. No.: 626,080

[22] Filed: Dec. 11, 1990

Related U.S. Application Data

[60] Division of Ser. No. 199,225, May 26, 1988, which is a division of Ser. No. 730,512, May 6, 1985, Pat. No. 4,759,789, which is a continuation-in-part of Ser. No. 490,055, Apr. 29, 1983, Pat. No. 4,566,901.

[30] Foreign Application Priority Data

May 6, 1982 [CH] Switzerland ............... 2804/82-3

[51] Int. Cl.⁵ ............... C07C 251/68; C07C 251/54; C07C 251/52; C07C 251/48
[52] U.S. Cl. ................. 564/254; 71/90; 71/92; 71/94; 71/95; 71/98; 71/100; 71/105; 71/106; 71/111; 544/159; 544/334; 544/335; 546/192; 546/216; 546/229; 546/232; 546/281; 546/300; 548/127; 548/201; 548/248; 548/452; 548/477; 548/569; 549/40; 549/14; 549/425; 549/484; 549/491; 549/551; 558/392; 558/393; 560/22; 560/35; 562/440; 564/44; 564/74; 564/149; 564/150; 564/162; 564/163; 564/166; 564/168; 564/255; 564/256
[58] Field of Search ............... 564/256, 154, 255

[56] References Cited

U.S. PATENT DOCUMENTS 4,117,154 9/1978 Stetter et al. ............... 564/255
4,474,815 10/1984 Holan et al. ............... 564/256

FOREIGN PATENT DOCUMENTS 1207788 10/1970 United Kingdom ............... 564/255

OTHER PUBLICATIONS

Martin, H. et al., "Oxime Ethers, Agents Containing Them & Their Use", CA, 100, 102946p, 1984.

Primary Examiner—Richard L. Raymond
Assistant Examiner—Susan P. Treanor
Attorney, Agent, or Firm—Edward McC. Roberts

[57] ABSTRACT

The invention relates to novel oxime ethers of the formula I

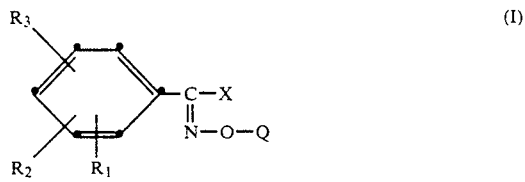

wherein $R_1$ is hydrogen, halogen, lower alkyl, lower haloalkyl, lower alkoxy, lower haloalkoxy, lower alkylthio, lower haloalkylthio, lower alkylsulfinyl, lower alkylsulfonyl, lower haloalkylsulfinyl, lower haloalkylsulfonyl or nitro, each of $R_2$ and $R_3$ is hydrogen, halogen, lower alkyl, lower alkoxy or lower haloalkoxy, and Q is an unsubstituted or substituted lower alkyl, lower alkenyl, lower alkynyl or cycloalkyl group, a lower alkanoyl radical, an aliphatic, cycloaliphatic, aromatic or heterocyclic acyl radical which may be substituted or unsubstituted, a carbonyl or thiocarbonyl radical, an aryl or aralkyl radical, an acylimidomethyl radical, a phthalimidomethyl radical or a heterocyclic radical.

These compounds are able to act as antidotes or safeners for protecting cultivated plants from the phytotoxic action of aggressive herbicides. Preferred crops are sorghum, cereals, maize and rice, and herbicides are chiefly chloroacetanilides and thiocarbamates.

15 Claims, No Drawings

NOVEL OXIME ETHERS, THE PREPARATION THEREOF, COMPOSITIONS CONTAINING THEM AND THE USE THEREOF

This is a divisional of application Ser. No. 199,225 filed on May 26, 1988 pending which is a divisional of Ser. No. 730.512 filed May 6, 1985, which is now U.S. Pat. No. 4,759,789, which is a continuation-in-part of Ser. No. 490,055, filed Apr. 29, 1983, which is now U.S. Pat. No. 4,566,901.

The present invention relates to novel oxime ethers, to the preparation thereof, to compositions for protecting cultivated plants from the phytotoxic effects of herbicides, which compositions contain the novel oxime ethers as active component, and to the use thereof.

It is known that herbicides belonging to a very wide range of compound classes such as triazines, urea derivatives, carbamates, thiocarbamates, haloacetanilides, halophenoxyacetic acids etc., when employed in an effective concentration, often also damage cultivated plants to a certain extent in addition to the weeds which it is desired to control. Too high concentrations are often applied unintentionally and randomly whenever peripheral zones overlap on zonal spraying, whether as a consequence of the action of wind or through miscalculating the sweep of the spray device employed. The climatic conditions or the nature of the soil may be such that the concentration of herbicide recommended for normal conditions acts as an overdose. The quality of the seeds may also be a factor in the tolerance of the herbicide. To counteract this problem, different compounds have already been proposed which are able specifically to antagonize the harmful action of the herbicide on the cultivated plant, i.e. to protect the cultivated plant without noticeably influencing the herbicidal action on the weeds to be controlled. However, it has been found that the proposed antidotes very often have a species-specific activity both with respect to the cultivated plants and to the herbicide and also, in some cases, contingent on the mode of application, i.e. a specific antidote is often suitable only for a specific cultivated plant and a few classes of herbicides.

For example, British patent specification 1 277 557 describes the protective treatment of seeds or seedlings of wheat and sorghum with certain oxamic acid esters and amides against attack by "ALACHLOR" (N-methoxymethyl-N-chloroacetyl-2,6-diethylaniline). Antidotes for treating cereals, maize and rice seeds against the harmful effects of herbicidal thiocarbamates are proposed in German Offenlegungsschrift specifications 1 952 910 and 2 245 471 and in French patent specification 2 021 611. German patent specification 1 576 676 and U.S. Pat. No. 3,131,509 disclose the use of hydroxyaminoacetanilides and hydantoins for protecting cereal seeds against the effects of carbamates.

The direct pre- or postemergence treatment of certain useful plants with antidotes as antagonists of specific classes of herbicides in a crop area is disclosed in German Offenlegungsschrift specifications 2 141 586 and 2 218 097 and in U.S. Pat. No. 3,867,444.

Further, German Offenlegungsschrift 2 402 983 discloses that maize plants can be effectively protected against damage by chloroacetanilides by adding an N-disubstituted dichloroacetamide as antidote to the soil.

According to German Offenlegungsschrift specification 2 808 317 and 2 837 204, alkoxyiminobenzylcyanides, in which the alkoxy group is differently substituted, can also be used as antidotes for protecting cultivated plants from the harmful effects of herbicides belonging to different classes of compounds.

The present invention relates to novel oxime ethers of the formula I

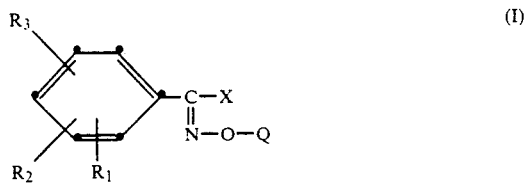

wherein
$R_1$ is hydrogen, halogen, lower alkyl, lower haloalkyl, lower alkoxy, lower haloalkoxy, lower alkylthio, lower haloalkylthio, lower alkylsulfinyl, lower alkylsulfonyl, lower haloalkylsulfinyl, lower haloalkylsulfonyl or nitro,
$R_2$ and $R_3$ are each hydrogen, halogen, lower alkyl, lower alkoxy or lower haloalkyl,
Q is lower alkyl which is straight chain or branched or interrupted by hetero atoms and is substituted
a) by halogen atoms or by the cyano or oxy group, or
b) by a phenoxy or thiophenoxy group, or is also lower alkenyl or haloalkenyl; lower alkynyl or haloalkynyl; a 3- to 7-membered cycloalkylcarbamoyl a lower alkanoyl radical; a lower alkenoyl radical; a lower alkyl carbamoyl or hydrazidocarbonyl radical; a lower alkyl thiocarbamoyl radical; a lower alkyl thiocarboxy radical; a lower alkanoyl radical or a salt thereof; an aliphatic or araliphatic acyl radical; a halogen-substituted aliphatic acyl radical; an aliphatic acyl radical which is substituted by alkoxy or phenoxy; a cycloaliphatic, aromatic or heterocyclic acyl radical; a substituted or unsubstituted aryl radical; an aliphatic, cycloaliphatic or aromatic carbonic acid radical; an aliphatic, cycloaliphatic or aromatic thiocarbonic acid radical; a carbamoyl radical; an alkyl or arylsulfonyl radical; an alkoxyalkylsulfamoyl or sulfamoyl radical; a halogen-substituted alkylsulfonyl or arylsulfonyl radical; a cyclic acylamidomethyl radical

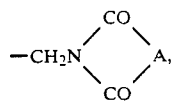

wherein A is an alkylene chain, a halogenated alkylene chain, an alkenyl chain or a halogenated alkenyl chain; a phthalimidomethyl radical which may be partially or completely saturated and may be substituted in the phenyl nucleus as indicated for $R_1$, $R_2$ and $R_3$; a 5- or 6-membered saturated, partially saturated or aromatic heterocyclic ring which may contain 1 to 3 nitrogen, oxygen and/or sulfur atoms and may be substituted as indicated for $R_1$, $R_2$ and $R_3$; and
X is a fluorinated $C_1$–$C_3$ alkyl radical which may also contain chlorine.
Halogen denotes fluorine, chlorine, bromine and iodine, with fluorine and chlorine being preferred.

The fluorinated alkyl radical X may be e.g. difluoromethyl, trifluoromethyl, chlorodifluoromethyl, tetrafluoroethyl, pentafluoroethyl, difluorochlorofluoroethyl and heptafluoropropyl. Among these radicals X, perfluorinated alkyl radicals are preferred in which one fluorine atom may be replaced by a chlorine atom. Particularly preferred radicals X are trifluoromethyl, chlorodifluoromethyl, pentafluoroethyl and difluoromethyl.

Alkyl by itself or as moiety of another substituent comprises branched or unbranched $C_1$–$C_8$ alkyl groups. Lower alkyl is $C_1$–$C_4$alkyl, e.g. methyl, ethyl, propyl, isopropyl, butyl, isobutyl, sec-butyl, tertbutyl, as well as the higher homologues amyl, isoamyl, hexyl, heptyl, octyl and the isomers thereof. By analogy, alkanoyl or cyanoalkyl groups contain an additional carbon atom. A lower alkanoyl radical consists of a lower alkyl moiety containing 1 to 4 carbon atoms, the carbonyl group and an alcoholic or phenolic radical of 1 to 8 carbon atoms. Examples are in particular: acetic acid esters —$CH_2$—COO—$C_1$–$C_8$-alkyl, —$CH_2$—CO—$C_3$–$C_4$alkenyl, —$CH_2$—COO—$C_3$–$C_4$-alkynyl or —$CH_2$—OO—phenyl, wherein the phenyl radical may be substituted by $R_1$, $R_2$ and $R_3$, and also $CH_2$—CO—S—$CH_1$–$C_8$alkyl, —$CH_2$—COS—$C_3$–$C_4$alkenyl or —$CH_2$—COS—$C_3$–$C_4$alkynyl, and also the corresponding 1-propionic acid esters —$CH(CH_3)$—COT (T = a $C_1$–$C_8$alkoxy, $C_1$–$C_8$alkylthio, $C_3$–$C_4$alkenyloxy, $C_3$–$C_4$alkenylthio, $C_3$–$C_4$alkynyloxy, $C_3$–$C_4$alkynylthio radical or a phenoxy radical which is unsubstituted or substituted by $R_1$, $R_2$ and $R_3$). Alkenyl radicals are aliphatic radicals containing one or two double bonds ("alkadienyl radicals") and a maximum of 6, preferably 4, carbon atoms. Haloalkenyl radicals contain up to 3 halogen atoms, preferably chlorine or bromine. Lower alkynyl is propynyl (=propargyl) and butynyl.

A lower alkenoyl radical consists accordingly of a lower alkenyl moiety containing 3 to 4 carbon atoms, the carbonyl group and an alcoholic or phenolic moiety containing 1 to 8 carbon atoms. Examples are in particular the butenoyl and pentenoyl radicals —$CH_2$—CH=CH—COT, $CH_2$—$CH(CH_3)$=CH—COT, $CH(CH_3)$=CH=CH—COT, wherein T is as defined above. A lower alkanoyl radical or a salt thereof consists of a lower alkyl moiety of 1 to 4 carbon atoms and the carboxyl group or a salt thereof with an alkali metal, alkaline earth metal, iron or copper ion or with the cation of a quaternary ammonium group.

Alkanecarbonamide radicals comprise also monosubstituted or symmetrically or unsymmetrically disubstituted radicals, the substituents of which may be selected from lower alkyl, lower alkenyl, propynyl or butynyl, as well as one cycloalkyl or phenyl ring which may be substituted as indicated for $R_2$/$R_3$ or unsubstituted. Examples of such radicals are the acetamido radical —$CH_2CONH_2$, the acetothiamido radical —$CH_2CSNH_2$, or the corresponding radicals in which one or both radicals are replaced by lower alkyl, lower alkenyl, lower alkynyl, cycloalkyl or phenyl, and also the corresponding propion-1-ylamido radicals —$CH(CH_3)CONH_2$ and propion-1-ylthioamido radical —$CH(CH_3)$—CS—$NH_2$. Also comprised are the acylated alkanecarbonamides radicals such as the acetoacetamide radical —$CH_2CONHCOCH_3$, the propion-1-ylacetamido radical —$CH(CH_3)CONHCOCH_3$, the acetoureido radical —$CH_2CONHCO$—$NH_2$, the propion-1-ylureido radical —$CH(CH_3)CONHCONH_2$, which radicals may be substituted symmetrically or unsymmetrically at the nitrogen atom by lower alkyl, lower alkenyl, lower alkynyl, cylcoalkyl or phenyl, and also the acetoformamido or propion-1-ylformamido radical and the acetohydrazido or propion-1-ylhydrazido radical.

An aliphatic, araliphatic, cycloaliphatic or aromatic acyl radical consists of a carbonyl group which is linked to a $C_1$–$C_8$alkyl group, a halogenated alkyl group, an alkoxy group, a halogenated alkoxy group, a $C_3$–$C_6$alkenyl group, a halogenated alkenyl group, an alkenyloxy group, a halogenated alkenyloxy group, a $C_3$–$C_6$alkynyl group, a halogenated alkynyl group, an alkynyloxy group, a halogenated alkynyloxy group, a $C_3$–$C_8$cycloalkyl group, a halogenated $C_3$–$C_8$cycloalkyl group, a halogenated cycloalkyl group or a phenyl group which is unsubstituted or substituted by $R_1$, $R_2$ and $R_3$. Representative examples of such radicals are: acetyl, propionyl, neopentamoyl, 1,1-dichloropropionyl, crotonyl, 2-methylcrotonyl, chloroacetyl, 1,1-dimethyl-2-chloropropionyl, dichloroacetyl, trifluoroacetyl, acroyl, methacroyl, dimethylacroyl, 1,2,2-trichloroacroyl, dibromoacroyl, α-bromoacroyl, methyloxalyl, ethyloxolyl, amidooxalyl, methoxyacetal, phenoxyacetyl, 1-(phenoxy)-propionyl, 1-(4-chlorophenoxy)propionyl, 1-(2-chlorophenoxy)propionyl, 1-(2,4-dichlorophenoxy)propionyl, 1-(4-chloro-2-methylphenoxy)propionyl, phenylthioacetyl, 1-(4-chlorophenylthio)acetyl, phenylacetyl, 4-chlorophenylacetyl, 3-methyl-1-phenylbutyryl, 3-methyl-1-p-chlorophenylbutyryl, 2,2-dimethylcyclopropylcarbonyl, cyclopropylcarbonyl, 2,2-dichlorocyclopropylcarbonyl, 1-methylcyclopropylcarbonyl, cyclopentylcarbonyl, cyclohexylcarbonyl, benzoyl, 2-methylbenzoyl, 3-trifluoromethylbenzoyl, 2-trifluoromethylbenzoyl, 4-difluorochloromethylbenzoyl, 2-nitrobenzoyl, 4-chlorobenzoyl, 3-chlorobenzoyl, 4-amisoyl, 3-acetoxybenzoyl, 3-methyl-4-nitrobenzoyl.

A heterocyclic acyl radical consists of the carbonyl group which is linked to a heterocyclic radical. Such radicals are saturated, partially saturated or heteroaromatic 5- or 6-membered radicals which contain 1 to 3 nitrogen, oxygen or sulfur atoms and which may be substituted by halogen atoms, lower alkyl, or as indicated for $R_1$, $R_2$ and $R_3$, and which may also contain oxo or sulfoxo groups.

Examples of such radicals are: nicotinoyl, isonicotinoyl, 1,3-dichloro-4-pyridinecarbonyl; thiophene-2-carbonyl; 2-furoyl, 4-methyl-1,2,3-thiadiazol-5-carbonyl, 4-(2,5-dimethyl)furoyl, 4-(3,5-dimethyloxazole)carbonyl, 3-(2-methyl-2,3-dihydro-4(H)-pyran)carbonyl, 2-(3methyl-3,4-dihydro-1,4-thioxan)carbonyl, 2-(3-methyl-3,4-dihydro-1-oxo-1,4-thioxan)carbonyl, 2-(2,4-dimethylthiazole)carbonyl, 2-thiazolecarbonyl, 4-(2,4-dichloropyrimidine)carbonyl, 2-(3-bromo)furoyl, 2-(4-nitro)furoyl, 2-(3-methyl)furoyl, 2-(3-chloro)thiophenecarbonyl, 4-pyridazinocarbonyl, 4-piperidinocarbonyl, 2-(4-methyl)-piperidinocarbonyl, 2-morpholinocarbonyl, 2-thiomorpholinocarbonyl, 2-pyrrolocarbonyl, 2-tetrahydrofuroyl, 2-oxazoyl, 3-pyrazolylcarbonyl, 2-pyrrolocarbonyl, 2-pyrrolidinocarbonyl.

$C_3$–$C_7$Cylcoalkyl groups are cyclopropyl, cyclobutyl, cyclopentyl, cyclohexyl and cycloheptyl. Cycloaliphatic radicals correspond to these ring systems but, where possible, may also additionally contain one or more double bonds.

An araliphatic radical comprises an aryl group such as phenyl which is mono- to trisubstituted as indicated for $R_1$, $R_2$ and $R_3$, or also naphthyl, fluorenyl or indanyl which is linked through lower alkyl or lower alkenyl to the residue of the molecule. Examples are benzyl, phenethyl, phenylallyl, 4-chlorobenzyl, 3,4-chlorobenzyl, 3-trifluorobenzyl, 2-chlorobenzyl, 3-chlorobenzyl, 3-bromobenzyl, 4-cyanobenzyl, 4-methylbenzyl, 4-tert-butylbenzyl, 2-fluorobenzyl, 2-fluorophenylethyl, 2-nitrobenzyl, 4-methoxybenzyl, 3-methoxybenzyl, 4-phenylbenzyl, 4-fluorobenzyl.

Examples of aliphatic chains interrupted by hetero atoms are methoxyethyl, ethoxyethyl, propoxyethyl, butoxyethyl, propoxyethyl, butoxyethyl, methoxypropyl, methylthioethyl, ethylthioethyl, methylthiopropyl, methylaminoethyl, tert-butylaminoethyl, methoxyethoxyethyl, ethoxyethoxyethyl.

A carbamoyl radical or a thiocarbamoyl radical carries at the nitrogen atom either hydrogen or one or two radicals selected from the group consisting of lower alkyl, lower alkoxyalkyl, lower alkenyl, lower haloalkenyl, alkynyl or a hydrogen atom, and alternatively a $C_3$-$C_6$cycloalkyl ring or a phenyl ring which may be substituted as indicated for $R_1$, $R_2$ and $R_3$ or unsubstituted. Examples of such radicals are: carbamoyl, methylcarbamoyl, ethylcarbamoyl, cyclohexylcarbamoyl, n-propylcarbamoyl, anilido, 2,6-dimethylanilido, 4-chloroanilido, 4-methoxyanilido, 3-trifluoromethylanilido, isopropylcarbamoyl, tert-butylcarbamoyl, thioanilido, 4-methylthioanilido.

A sulfoxyl radical consists of the sulfoxy group and an unsubstituted or halogenated $C_1$-$C_8$alkyl radical or a phenyl radical which may be substituted as indicated for $R_1$, $R_2$ and $R_3$. Examples of such radicals are methylsulfonyl, chloromethylsulfonyl, trifluoromethylsulfonyl, phenylsulfonyl, 4-chlorophenylsulfonyl, 4-tolylsulfonyl, 4-trifluoromethylphenylsulfonyl, trichloromethylsulfonyl.

A sulfamoyl radical carries at the nitrogen atom either hydrogen or preferably two radicals selected from the group consisting of lower alkyl, lower alkoxyalkyl, lower alkenyl or $C_4$-$C_5$alkylene which may be interrupted by oxygen or sulfur. Examples of such radicals are: dimethylsulfamoyl, piperidinosulfonyl, morpholidosulfonyl.

A cyclic acylamidomethyl radical consists of the dicarbonylimidomethylene moiety and an alkylene, halogenated alkylene, alkenylene or halogenated alkenylene chain. Examples of such radicals are malonylimidomethyl, maloylimidomethyl, succinylimidomethyl, glutanylimidomethyl, fumaroylimidomethyl, 2,3-dimethylfumaroylimidomethyl, 2,3-dichlorofumaroylimidomethyl.

The phthalimidomethyl radicals may be both substituted in the phenyl nucleus as indicated for $R_1$, $R_2$ and $R_3$ and partially or completely saturated, and are accordingly 3,4-dihydrophthalimidomethyl and tetrahydrophthalimidomethyl radicals.

Heterocyclic radicals are monocyclic and bicyclic rings containing 1 to 3 identical or different hetero atoms O, S and N. Representative examples are 3- to 6-membered, preferably 5- or 6-membered, heterocyclic rings which may be saturated, partially saturated or unsaturated and substituted as indicated for $R_1$, $R_2$ and $R_3$ or unsubstituted. Without implying any limitation, representative examples of such rings are: furan, nitrofuran, bromofuran, methylfuran, thiophene, chlorothiophene, pyridine, 2,6-dichloropyridine, pyrimidine, pyridazine, pyrazine, piperidine, methylpiperidine, morpholine, thiomorpholine, tetrahydrofuran, oxazole, pyrazole, pyrrole, pyrroline, pyrrolidine, thiazole, 2,3-dihydro-4-H-pyrane, pyrane, dioxan, 1,4-oxathia(2)-ine, quinoline, indole, benzthiazole, benzoxazole, benzimidazole.

Particularly important oximes of this invention are the compounds of the formula Ia

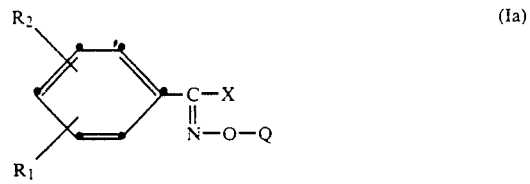

wherein $R_1$, $R_2$, Q and X are as defined for formula I. Among this group of oximes, those compounds are especially preferred in which X is the trifluoromethyl group and which have the formula Ib

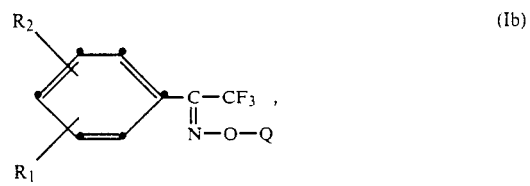

wherein $R_1$, $R_2$ and Q are as defined for formula I. Oxime ethers having pronounced biological properties are those of the formula Ic

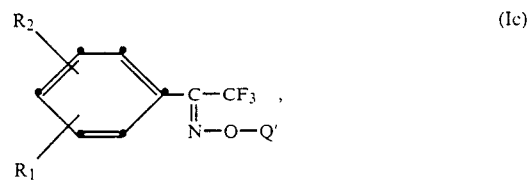

wherein $R_1$ and $R_2$ are as defined for formula I and Q' is $C_1$-$C_4$alkyl, preferably methyl, ethyl, Propyl and butyl and also cyclopropyl, $C_3$-$C_4$alkenyl such as allyl, $C_1$-$C_4$cyanoalkyl such as cyanomethyl and cyanoeth-1-yl, carbamoyl, $C_1$-$C_4$carbamoylalkyl such as carbamoylmethyl or carbamoyleth-1-yl, $C_1$-$C_4$alkylcarbamoyl, di($C_1$-$C_4$alkyl)carbamoyl.

Preferred individual compounds are in particular:
1-phenyl-1 methoximino 2,2,2-trifluoroethane,
1-(3-trifluoromethylphenyl-1-cyclopropylmethoximino-2,2,2-trifluoroethane,
1-(4-chlorophenyl)-1-n-propoximino-2,2,2-trifluoroethane,
1-(4-chlorophenyl)-1-allyloximino-2,2,2-trifluoroethane,
1-phenyl-1-carbamoylmethoximino-2,2,2-trifluoroethane,
1-(4-fluorophenyl)-1-carbamoylmethoximino-2,2,2-trifluoroethane,
1-(4-chlorophenyl)-1-carbamoylmethoximino-2,2,2-trifluoroethane,
1-(3-trifluoromethyl) 1-carbamoylmethoximino-2,2,2-trifluoroethane,
1-phenyl-1-carbamoylmethoximino-2,2,3,3,3-pentafluoropropane,
1-phenyl-1-carbamoyleth-1-oximino-2,2,2-trifluoroethane,
1-(4-chlorophenyl)-1-carbamoyleth-1'oximino-2,2,2-trifluoroethane, 1-(3-trifluoromethylphenyl)-1-carbamoyleth-1'-oximino-2,2,2-trifluoroethane,
1-(4-chlorophenyl-1-N-n-propylcarbamoyloximino-2,2,2-trifluoroethcne,
1-(3-chlorophenyl)-1-carbamoylmethoximino-2,2,2-trifluoroethane,
1-(3-chlorophenyl)-1-isopropyloxycarbamoylmethoximino-2,2,2-trifluoroethane.

The novel oxime ethers of this invention are prepared by reacting a salt of an oxime of the formula II

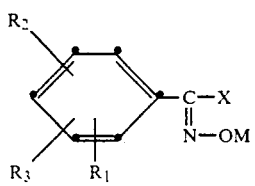   (II)

wherein M is an alkali metal cation or an alkaline earth metal cation and $R_1$, $R_2$, $R_3$ and X are as defined above, with a reactive ester of the formula III $$Y-Q \quad \text{(III)}$$

wherein Q is as defined for formula I and Y is the radical of an organic or inorganic acid.

Suitable salts of an oxime of the formula II are in particular the sodium and potassium salts. The reaction of the oxime of the formula II with the reactive ester of the formula III is conveniently carried out in an inert organic solvent. Particularly suitable solvents are polar solvents such as acetonitrile, dimethylformamide, dimethylacetamide, methylpyrrolidone and dimethylsulfoxide. The reactants are normally employed in equimolar amount. However, an excess of one or other reactant may also be used to bring the reaction to completion. Particularly suitable reactive acid radicals are the halides and also sulfonic acid radicals of e.g. methylsulfonic acid, ethylsulfonic acid, phenylsulfonic acid or toluenesulfonic acid. The reaction is conveniently carried out in the temperature range from 60° to 90° C. If another solvent is used, e.g. toluene or chlorobenzene, then the reaction is carried out at higher temperature and the reaction time is longer.

According to U.S. Pat. No. 4,260,555, the radical Q is esterified with a sulfonic acid radical and the resultant ester of the formula IV $$Z-SO_3-Q \quad \text{(IV)}$$

wherein Z is a lower alkyl radical or a phenyl radical substituted by lower alkyl or halogen, is reacted with the hydroxyoxime of the formula II or a salt thereof.

The oximes of formula II may be prepared in known manner by reacting the corresponding ketones with hydroxylamine. The ketones required for the reaction can in turn be obtained by reacting a Grignard compound of the formula V

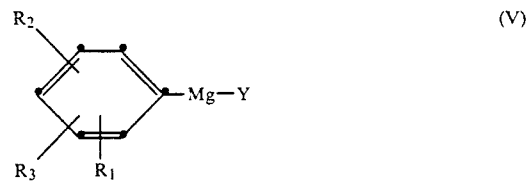   (V)

wherein Y is chlorine, bromine or iodine, and $R_1$, $R_2$ and $R_3$ are as defined above, with a carboxylic acid X—COOH or a salt thereof, an acid chloride X—COCl or a nitrile X—CN, each derived from the radical X as defined above (cf. U.S. Pat. No. 3,748,361). Further, it is also possible to obtain ketones suitable for preparing the oximes of formula II by reacting a benzene of the formula VI

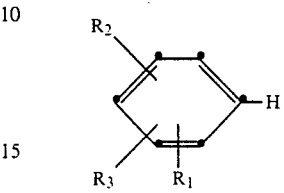

in which $R_1$, $R_2$ and $R_3$ are as defined above, with a carboxylic acid chloride X—COCl derived from the radical X as defined above, in the presence of aluminium chloride.

Examples of oximes of the formula II which are suitable for obtaining the novel oxime ethers of the formula I are:
1-phenyl-1-hydroximino-2,2,2-trifluoroethane
1-(4-methylphenyl)-1.hydroximino-2,2,2-trifluoroethane
1-(4-chlorophenyl)-1-hydroximino-2,2,2-trifluoroethane
1-(4-fluorophenyl)-1-hydroximino-2,2,2-trifluoroethane
1-(4-trifluoromethylphenyl)-1-hydroximino-2,2,2-trifluoroethane
1-(3-trifluoromethylphenyl)-1-hydroximino-2,2,2-trifluoroethane
1-(4-methoxyphenyl)-1-hydroximino-2,2,2-trifluoroethane
1-(4-trifluoromethoxyphenyl)-1-hydroximino-2,2,2-trifluoroethane
1-(3-nitrophenyl)-1-hydroximino-2,2,2-trifluoroethane
1-(3,4-dimethylphenyl)-1-hydroximino-2,2,2-trifluoroethane
1-(3,4-dichlorophenyl)-1-hydroximino-2,2,2-trifluoroethane
1-(4-chlorophenyl)-1-hydroximino-2,2-difluoroethane
1-(4-chlorophenyl)-1-hydroximino-2-chloro-2,2-difluoroethane
1-(4-methoxyphenyl)-1-hydroximino-2-chloro-2,2-difluoroethane
1-(4-trifluoromethoxyphenyl)-1-hydroximino-2-chloro-2,2-difluoroethane
1-(3-nitrophenyl)-1-hydroximino-2-chloro-2,2-difluoroethane
1-phenyl-1-hydroximino-2,2,3,3,3-pentafluoropropane
1-(4-methylphenyl)-1-hydroximino-2,2,3,3,3-pentafluoropropane
1-(4-chlorophenyl)-1-hydroximino-2,2,3,3,3-pentafluoropropane
1-(3-nitrophenyl)-1-hydroximino-2,2,3,3,3-pentafluoropropane
1-phenyl-1-hydroximino-2,2,3,3,4,4,4-heptafluorobutane
1-(4-chlorophenyl)-1-hydroximino-2,2,3,3,4,4,4-heptafluorobutane
1-(2-chlorophenyl)-1-hydroximino-2,2,2-trifluoroethane
1-(3-chlorophenyl)-1-hydroximino-2,2,2-trifluoroethane.

Suitable reactive esters of the formula III are in particular the halides and sulfonic acid esters corresponding to the definition of Q, substituted lower alkyl groups, lower alkenyl or alkynyl groups or cycloalkyl groups, and also alkanecarboxylic acid derivatives which are halogenated or sulfonated in the alkyl moiety; and arylhalides, arylsulfonates, aralkylhalides or aralkylsulfonates; the halides of carbonic acid esters or thiocarbonic acid esters, alkylsulfonyl or arylsulfonyl halides, or a halide of a sulfamoyl group; and also the halomethyl or sulfonylmethyl derivatives of acyliminomethyl or phthalimidomethyl groups; and halides or sulfonyl esters of heterocyclic radicals which correspond to the definition of Q.

Such compounds are known or may be prepared e.g. by reaction with halogenating agents such as sulfuryl chloride or sulfuryl bromide, thionyl chloride or thionyl bromide, phosphoroxy chloride or phosphoryl ester chloride or the corresponding bromides, or with a concentrated hydrohalic acid or by reaction with halides or anhydrides of sulfonic acids.

The novel oxime ethers of formula I are most suitable for protecting cultivated plants from damage caused by agrochemicals. This protection extends in particular to herbicides of different compound classes, including 1,3,5-triazines, 1,2,4-triazines, phenylurea derivatives, carbamates, thiocarbamates, phenoxyacetates, phenoxypropionates, haloacetanilides, halophenoxyacetates, substituted phenoxyphenoxyacetates and phenoxyphenoxypropionates, substituted pyridyloxyphenoxyacetates and pyridyloxyphenoxypropionates, benzoic acid derivatives etc., where these compounds are not tolerated or are insufficiently tolerated by cultivated plants. The novel oxime ethers of formula I are suitable in particular for protecting cultivated plants from the harmful effects of haloacetanilides and thiocarbamates. They can therefore be termed antidotes or also safeners with respect to their use in combination with the herbicides referred to above.

The compounds of the formula I exist in different stereoisomeric forms, viz. the syn- and anti-forms of the basic oximes and also individual enantiomers of such compounds which contain a centre of asymmetry in the radical Q. These stereoisomers also fall within the province of the invention.

Depending on the end use, the safener or antidote of the formula I can be used for pretreating seeds of the cultivated plant (dressing of the seeds or seedlings) or it can be added to the soil before or after sowing. However, it can also be applied pre- or postemergence by itself alone or together with the herbicide. The treatment of the plant or seeds with the antidote can therefore in principle be carried out independently of the time of application of the phytotoxic chemical. It can, however, also be carried out by simultaneous application of phytoxic chemical and antidote (tank mixture). The pre-emergence treatment includes both treatment of the crop area before sowing (ppi=pre-plant incorporation) and treatment of the crop areas after sowing but before emergence of the plants.

The rates of application of the antidote with respect to the herbicide depend largely on the mode of application. Where a field treatment is carried out, either simultaneously as tank mixture or with separate application of herbicide and antidote, the ratio of antidote to herbicide is in the range from 1:100 to 5:1. Full protective action is usually obtained at a ratio of antidote to herbicide of 1:1 to 1:20. When dressing seeds and taking similar specific protective measures, however, much lower amounts of antidote are required compared with e.g. the amounts of herbicide later employed per hectare of crop area. For seed dressing, 0.1 to 10 g of antidote per kg of seeds are required. Full protection is usually obtained with 0.1 to 2 g of antidote per gram of seeds. If it is desired to apply the antidote shortly before sowing by seed pretreatment, antidote solutions which contain the active ingredient in a concentration of 1 to 10,000 ppm are used. Full protective action is normally obtained with antidote concentrations of 100 to 1000 ppm.

As a rule there is a substantial interval of time between protective measures such as seed dressing and treatment of seedlings with an antidote of the formula I and the possible later field treatment with agricultural chemicals. Pretreated seeds and plants can later come in contact with different chemicals in agriculture, horticulture and forestry. Accordingly, the invention relates to plant protection compositions which contain an antidote of the formula I as active ingredient, together with conventional carriers. If appropriate, such compositions may be additionally mixed with the chemical against whose effects it is desired to protect the cultivated plant.

Cultivated plants within the scope of this invention are all plants which, in any form, can be harvested (seeds, roots, stalks, tubers, leaves, blossoms) and from which extracts can be obtained (oils, sugar, starch, protein) and which are cultivated for this purpose. These plants comprise e.g. all species of cereals such as wheat, rye, barley, oats and, in particular, rice, sorghum, maize, and also cotton, sugar beet, sugar cane, soybeans, beans, and peas.

The antidote can be employed wherever it is desired to protect a cultivated plant of the kind indicated above from the harmful effects of an agricultural chemical. As already mentioned, possible agricultural chemicals are primarily herbicides of the most widely varying compound classes, in particular haloacetanilides and thiocarbamates.

Numerous haloacetanilides whose harmful effects on cultivated plants can be antagonised with the novel oxime ethers of the formula I are known in the art (q.v. German patent applications 2 305 495, 2 328 340, 2 212 268, 2 726 252 and 2 805 757, and U.S. Pat. Nos. 3,946,044, 4,022,608 and 4,039,314). Such haloacetanilides may be illustrated by the general formula VII

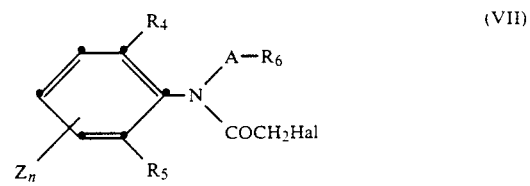

(VII)

wherein Hal is halogen, preferably chlorine or bromine, each of $R_4$ and $R_5$ independently of the other is hydrogen, halogen, lower alkyl, alkoxy, alkylthio, haloalkyl, alkoxyalkyl or alkylthioalkyl, Z is hydrogen, halogen, lower alkyl, alkoxy, alkylthio, haloalkyl, alkoxyalkyl or alkylthioalkyl, which radicals Z are preferably in the 3-position with respect to the nitrogen atom, n is 0 to 3, A is alkylene, preferably methylene, 1,1-ethylene, and 1,2-ethylene which may be substituted by 1 or 2 lower alkyl groups, and $R_6$ is lower alkoxy, hydroxycarbonyl, alkoxycarbonyl, carbamoyl, N-alkylcarbamoyl, N,N- dialkylcarbamoyl, cyano, an unsubstituted or substituted nitrogen-containing heterocyclic radical, alkanoyl, unsubstituted or substituted benzoyl, unsubstituted or substituted 1,3,4-oxadiazol-2-yl, 1,3,4-thiadiazol-2-yl, 1,3,4-triazol-3-yl or 1,3,4-triazol-1-yl.

Typical examples of such haloacetanilides are:
N-ethoxymethyl-N-chloroacetyl-2-ethyl-6-methylaniline
N-chloroacetyl-N-methoxymethyl-2,6-diethylaniline
N-chloroacetyl-N-(2-methoxyethyl)-2,6-dimethylaniline
N-(2-allyloxyethyl)-N-chloroacetyl-2,6-dimethylaniline
N-chloroacetyl-N-(2-n-propoxyethyl)-2,6-dimethylaniline
N-chloroacetyl-N-(2-isopropoxyethyl)-2,6-dimethylaniline
N-chloroacetyl-N-(2-methoxyethyl)-2-ethyl-6-methylaniline
N-chloroacetyl-N-(methoxyethyl)-2,6-diethylaniline
N-(2-ethoxyethyl)-N-chloroacetyl-2-ethyl-6-methylaniline
N-chloroacetyl-N-(2-methoxy-1-methylethyl)-2-methylaniline
N-chloroacetyl-N-(2-methoxy-1-methylethyl)-2,6-dimethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-methoxycarbonylmethyl-2,6-dimethylaniline
N-chloroacetyl-N-(2,2-diethoxyethyl)-2,6-dimethylaniline
N-chloroacetyl-N-(2-methoxy-1-methylethyl)-2,3-dimethylaniline
N-(2-ethoxyethyl)-N-chloroacetyl-2-methylaniline
N-chloroacetyl-N-(2-methoxyethyl)-2-methylaniline
N-chloroacetyl-N-(2-methoxy-2-methylethyl)-2,6-dimethylaniline
N-(2-ethoxy-2-methylethyl)-N-chloroacetyl-2-ethyl-6-methylaniline
N-chloroacetyl-N-(1-ethyl-2-methoxyethyl)-2,6-dimethylaniline
N-chloroacetyl-N-(2-methoxyethyl)-2-methoxy-6-methylaniline
N-n-butoxymethyl-N-chloroacetyl-2-tert-butylaniline
N-(2-ethoxyethyl-1-methylethyl)-2,6-dimethylaniline
N-chloroacetyl-N-(2-methoxyethyl)-2-chloro-6-methylaniline
N-(2-ethoxyethyl)-N-chloroacetyl-2-chloro-6-methylaniline
N-(2-ethoxyethyl)-N-chloroacetyl-2,3,6-trimethylaniline
N-chloroacetyl-1-(2-methoxyethyl)-2,3,6-trimethylaniline
N-chloroacetyl-N-cyanomethyl-2,6-dimethylaniline
N-but-3-yn-1-yl-N-chloroacetylaniline
N-chloroacetyl-N-propargyl-2-ethyl-6-methylaniline
N-chloroacetyl-N-(1,3-dioxolan-2-ylmethyl)-2,6-dimethylaniline
N-chloroacetyl-N-(1,3-dioxolan-2-ylmethyl)-2-ethyl-6-methylaniline
N-chloroacetyl-N-(1,3-dioxan-2-ylmethyl)-2-ethyl-6-methylaniline
N-chloroacetyl-N-(1,3-dioxan-2-ylmethyl)-2-ethyl-6-methylaniline
N-chloroacetyl-N-(2-furanylmethyl)-2,6-dimethylaniline
N-chloroacetyl-N-(2-furanylmethyl)-2-ethyl-6-methylaniline
N-chloroacetyl-N-(2-tetrahydrofuranylmethyl)-2,6-dimethylaniline
N-chloroacetyl-N-(N-propargylcarbamoylmethyl)-2,6-dimethylaniline
N-chloroacetyl-N-(N,N-dimethylcarbamoylmethyl)-2,6-dimethylaniline
N-(n-butoxymethyl)-N-chloroacetyl-2,6-diethylaniline
N-(2-n-butoxyethyl)-N-chloroacetyl-2,6-diethylaniline
N-chloroacetyl-N-(2-methoxy-1,2-dimethylethyl)-2,6-dimethylaniline
N-chloroacetyl-N-isopropyl-2,3-dimethylaniline
N-chloroacetyl-N-isopropyl-2-chloroaniline
N-chloroacetyl-N-(1H-pyrazol-1-ylmethyl)-2,6-dimethylaniline
N-chloroacetyl-N-(1H-pyrazol-1-ylmethyl)-2-ethyl-6-methylaniline
N-chloroacetyl-N-(1H-1,2,4-triazol-1-ylmethyl)-2,6-dimethylaniline
N-chloroacetyl-N-(1H-1,2,4-triazol-1-ylmethyl)-2,6-diethylaniline
N-benzoylmethyl-N-chloroacetyl-2,6-dimethylaniline
N-benzoylmethyl-N-chloroacetyl-2-ethyl-6-methylaniline
N-chloroacetyl-N-(5-methyl-1,3,4-oxadiazol-2-yl)-2,6-diethylaniline
N-chloroacetyl-N-(5-methyl-1,3,4-oxadiazol-2-yl)-2-ethyl-6-methylaniline
N-chloroacetyl-N-(5-methyl-1,3,4-oxadiazol-2-yl)-2-tert-butylaniline
N-chloroacetyl-N-(4-chlorobenzoylmethyl)-2,6-dimethylaniline
N-chloroacetyl-N-(1-methyl-5-methylthio-1,3,4-triazol-2-ylmethyl)-2,6-diethylaniline.

Further haloacetanilides whose harmful effects on cultivated plants can be antagonised by the novel oxime ethers of the formula I are listed in R. Wegler, Chemie der Pflanzenschutz- und Schädlingsbekämpfungsmittel, Vol. 8, pp. 90–93 and pp. 322–327.

Numerous herbicidal thiocarbamates whose phytotoxic action on cultivated plants can be antagonised by the novel oxime ethers of the formula I are also known (q.v. for example U.S. Pat. Nos. 2,913,327, 3,037,853, 3,175,897, 3,185,720, 3,198,786, 3,582,314 and 3,846,115). The protective action of the novel oxime ethers of the formula I can be utilised particularly when applying thiocarbamates in cereals, rice or sorghum.

The thiocarbamates against whose phytotoxic action cultivated plants such as cereals, rice and sorghum may particularly be protected, have the general formulae VIII and IX

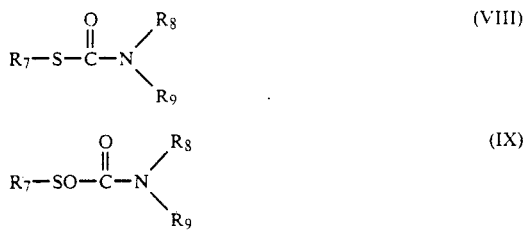

wherein $R_7$ is lower alkyl, alkenyl, chloroallyl, dichloroallyl, trichloroallyl, benzyl or 4-chlorobenzyl, $R_8$ is $C_2$–$C_4$ alkyl and $R_9$ is $C_2$–$C_4$ alkyl or cyclohexyl, and $R_8$ and $R_9$ together with the nitrogen atom to which they are attached can form a hexahydro-1H-azepine, decahydroquinoline or 2-methyldecahydroquinoline ring.

Typical individual representatives of such thiocarbamates are:
S-ethyl-N,N-dipropylthiocarbamate
S-ethyl-N,N-diisobutylthiocarbamate
S-2,3-dichloroallyl-N,N-diisopropylthiocarbamate
S-propyl-N-butyl-N-ethylthiocarbamate
S-2,3,3-trichloroallyl-N,N-diisopropylthiocarbamate
S-propyl-N,N-dipropylthiocarbamate
S-ethyl-N-ethyl-N-cyclohexylthiocarbamate
S-ethyl-N-hexahydro-1H-azepine-1-carbothioate
S-isopropyl-N,N-hexamethylene-thiocarbamate
S-(p-chlorobenzyl)-N,N-diethylthiocarbamate
N-ethylthiocarbonyl-cis-decahydroquinoline
N-propylthiocarbonyl-decahydroquinaldine
S-ethyl-N,N-bis(n-butyl)-thiocarbamate
S-tert-butyl-N,N-bis(n-propyl)-thiocarbamate.

The amount of antidote employed varies from about 0.01 to about 15 parts by weight per part by weight of herbicide. The most suitable ratio in respect of optimum action on the particular cultivated plant is established from case to case, i.e. depending on the type of herbicide employed.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Inc. New York, 1964.

The pesticidal formulations usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (% =percentage by weight):

Emulsifiable concentrates active ingredient: 1 to 20%, preferably 5 to 10%
surfactant: 5 to 30%, preferably 10 to 20%
liquid carrier: 50 to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 5 to 90%, preferably 1 to 80%,
surfactant: 0.5 to 20%, preferably 1 to 15%
solid carrier: 5 to 95%, preferably 15 to 90%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.1 to 10 kg a.i./ha, preferably 0.025 to 5 kg a.i./ha.

The compositions may also contain further ingredients such as stabilisers, antifoams, viscosity regulators, binders, adhesives, as well as fertilisers or other active compounds, in order to attain special effects.

The invention is illustrated in more detail by the following Examples.

EXAMPLE 1

Preparation of
1-phenyl-1-cyanomethoximino-2,2,2-trifluoroethane
(compound 4)

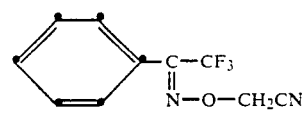

19 g (0.1 mol) of 1-(hydroximino)-1-phenyl-2,2,2-trifluoroethane are stirred into a solution of 2.3 g (0.1 mol) and the solvent is removed by evaporation. The residue is dissolved in 50 ml of dimethylsulfoxide and 15.1 g (0.2 mole) of chloroacetonitrile are added dropwise to the solution. When the addition of chloroacetonitrile is complete, the reaction mixture is initially stirred for 4 hours at 60°-70° C. and then poured into ice/water. The organic phase is extracted with methylene chloride. The extract is dried and the solvent removed by evaporation, affording 12.1 g (53.1% of theory) of crystalline title compound, which has a melting point of 54°-56° C. after recrystallisation from isopropanol.

Analysis: calculated C 52.64%; H 3.09%; N 12.38%; F 24.98%; found: C 52.3%; H 3.2%; N 12.4%; F 24.4%.

EXAMPLE 2

Preparation of
1-(4-chlorophenyl)-1-tetrahydrofurfuryl-2-methoxycarbonyl-methoximino-2,2,2-trifluoroethane (compound 312)

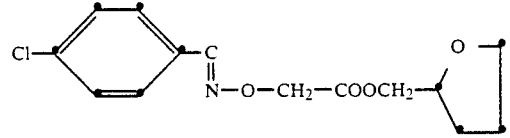

A solution of 15.7 g (0,07 mol) of 1-(hydroxyimino-1-(4-chlorophenyl-2,2,2-trifluoroethane in 70 ml of toluene in a 250 ml round-bottom-flask is added with 9,4 ml of 30% aqueous sodium hydroxide, stirred for a while and then evaporated to dryness in a rotatory evaporator. The residue is taken up in 50 ml of dimethylsulfoxide and 15.6 g (0,07 mol) of bromoacetic acid tetrahydrofuryl ester are added dropwise thereto. The reaction mixture is then stirred for 5 hours at 60-70°. The resulting suspension is poured onto ice/water and the organic material is extracted therefrom with methylene chloride. The organic layers are washed with water, dried over sodium sulfate, filtered and concentrated on a rotatory evaporator. The remaining oil is distilled under high vacuum to yield a clear oil boiling at 127-128°/0.03 mbar.

EXAMPLE 3

Preparation of 1-(3-trifluoromethylphenyl)-1-ethoxycarbonyl-methoximino)-2,2,2-trifluoroethane (compound 332)

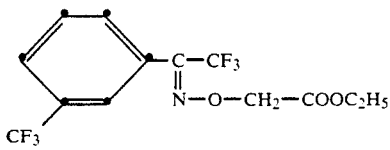

A solution of 12.9 g (0,05 mol) of 1-hydroxyimino-1-(3-trifluoromethylphenyl)-2,2,2-trifluoroethane in 70 ml of toluene in a 250 ml round-bottom-flask is added with 6.7 ml of 30% aqueous sodium hydroxide, stirred for a while and then evaporated to dryness in a rotatory evaporator. The residue is taken up in 50 ml of dimethylsulfoxide and 10.0 g (0,06 mol) of bromoacetic acid-ethyl ester are added dropwise thereto. The reaction mixture is then stirred for 5 hours at a temperature of 60-70°, before it is poured onto ice/water. The organic material is extracted from this mixture with methylene chloride. The methylene-chloride extracts are washed with water, dried over sodium sulfate, filtered and concentrated in a rotatory evaporator. The remaining oil is distilled under high vacuum and passes as a clear oil at 62-63°/0.06 mbar.

The following compounds are prepared in corresponding manner:

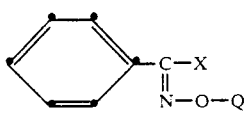

| No. | Phenyl substitution | X | Q | Physical data (°C.) |
|---|---|---|---|---|
| 1 | — | $CF_3$ | $CH_3$ | b.p. 30-31°/0.08 mbar |
| 2 | — | $CF_3$ | $C_3H_7n$ | b.p 40-41°/0.08 mbar |
| 3 | — | $CF_3$ | $CH_2C\equiv CH$ | b.p 50-54°/0.03 mbar |
| 4 | — | $CF_3$ | $CH_2CN$ | m.p. 54-56°(example 1) |
| 5 | — | $CF_3$ | $CH_2CONH_2$ | m.p. 84-86° |
| 6 | — | $CF_3$ | $CON(CH_3)CH_2CN$ | $n_D^{20}$ 1.4960 |
| 7 | — | $CF_3$ | $CONHCH_3$ | m.p. 94-96° |
| 8 | — | $CF_3$ | $COC(Cl)=C(Cl)_2$ | $n_D^{20}$ 1.5210 |
| 9 | — | $CF_3$ | $CONHC(CH_3)_3$ | m.p. 113-115° |
| 10 | — | $CF_3$ | $CH_2OCOC(CH_3)_3$ | b.p. 79-80°/0.07 mbar |
| 11 | 4-F | $CF_3$ | $CH_3$ | b.p. 63-64°/14 mbar |
| 12 | 4-F | $CF_3$ | $C_3H_7n$ | b.p. 82-84°/12 mbar |
| 13 | 4-F | $CF_3$ | $CH_2CN$ | b.p. 119-122°/12 mbar |
| 14 | 4-F | $CF_3$ | $CH_2CONH_2$ | m.p. 52-54° |
| 15 | 4-Cl | $CF_3$ | $CON(CH_3)CH_2CN$ | wax-like |
| 16 | 4-Cl | $CF_3$ | $CON(CH_3)C_2H_4CN$ | wax-like |
| 17 | 4-Cl | $CF_3$ | $COC_6H_4CH_3(2)$ | $n_D^{20}$ 1.5155 |
| 18 | 4-Cl | $CF_3$ | $COC_6H_4CF_3(3)$ | $n_D^{20}$ 1.4900 |
| 19 | 4-Cl | $CF_3$ | $CONHC(CH_3)_3$ | m.p. 121-122° |
| 20 | 4-Cl | $CF_3$ | $CONHCH_3$ | m.p. 85-89° |
| 21 | 4-Cl | $CF_3$ | $CH_2CN$ | oil $n_D^{24}$ = 1.4930 |
| 22 | 4-Cl | $CF_3$ | $COC_6H_5$ | |
| 23 | 3-Cl | $CClF_2$ | $CH_3$ | |
| 24 | — | $CClF_2$ | $C_3H_7n$ | |
| 25 | 4-Br | $CClF_2$ | $CH_2CH=CH_2$ | |
| 26 | 4-$NO_2$ | $CClF_2$ | $CH_3$ | |
| 27 | 4-$CF_3$ | $CF_3$ | $CH_2CN$ | |
| 28 | 4-$OCF_3$ | $CF_3$ | $CH_3$ | |
| 29 | 4-$C_4H_9$ | $CF_3$ | $CH_2CN$ | |
| 30 | — | $C_2F_5$ | $COC_6H_4Cl(4)$ | |
| 31 | — | $C_2F_5$ | $CH_3$ | |
| 32 | — | $C_2F_5$ | $CONH_2$ | |
| 33 | — | $C_2F_5$ | $CH_2CN$ | |
| 34 | 4-Cl | $C_2F_5$ | $CH_3$ | |
| 35 | 4-Cl | $C_2F_5$ | $CH_3$ | |
| 36 | 4-Cl | $C_2F_5$ | $COCH_3$ | |
| 37 | 4-$OCH_3$ | $CF_3$ | $CH_3$ | |
| 38 | 4-$OCH_3$ | $CF_3$ | $C_3H_7n$ | |
| 39 | 4-$OCH_3$ | $CF_3$ | $CH_2-CH=CH_2$ | |
| 40 | 4-$OCH_3$ | $CF_3$ | $CH_2CN$ | |
| 41 | 4-$OCF_3$ | $CF_3$ | $CH_3$ | |
| 42 | 4-$OCF_3$ | $CF_3$ | $CH_2CN$ | |
| 43 | 4-$OCF_3$ | $CF_2Cl$ | $C_3H_7n$ | |
| 44 | 3-Cl | $CF_3$ | $CH_3$ | |
| 45 | 2-Cl | $CF_3$ | $CH_2CN$ | 73-74° C./0.1 |
| 46 | 3-Cl | $CF_3$ | $CH_2CONH_2$ | |
| 47 | 3-Cl | $CF_3$ | $CH_2-CH=CH_2$ | |
| 48 | 3-$NO_2$ | $CF_3$ | $CH_2CN$ | |
| 49 | 3-$NO_2$ | $CF_3$ | $CH_2CONH_2$ | |
| 50 | 3-$NO_2$ | $CF_3$ | $CH_2C(CH_3)_3$ | |
| 51 | 3-$NO_2$ | $CF_3$ | $CH_2-CH=CH_2$ | |
| 52 | 2-Cl | $CF_3$ | $C_3H_7n$ | |
| 53 | 2-Cl | $CF_3$ | $C_2H_4CN$ | |
| 54 | 2-Cl | $CF_3$ | $CH_2-CCl=C(Cl)_2$ | |
| 55 | 3-$CF_3$ | $CF_3$ | $CH_2COOC(CH_3)_3$ | |

-continued

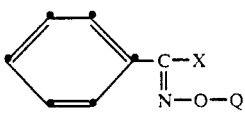

| No. | Phenyl substitution | X | Q | Physical data (°C.) |
|---|---|---|---|---|
| 56 | 4-Br | $CF_3$ | $C_3H_7i$ | |
| 57 | 4-Br | $CF_3$ | $CH_2C(CH_3)_3$ | |
| 58 | 4-Br | $CF_3$ | $CH_2CN$ | |
| 59 | 4-Br | $CF_3$ | $CH_2CONH_2$ | |
| 60 | 4-$CF_3$ | $CF_3$ | $CH_2CONHCH_3$ | |
| 61 | 4-$CF_3$ | $CF_3$ | $CH(CH_3)CN$ | |
| 62 | 4-$CF_3$ | $CF_3$ | $CH_2CONH_2$ | |
| 63 | 4-$CF_3$ | $CF_3$ | $CH_2C(CH_3)=CH_2$ | |
| 64 | 4-Cl | $CF_3$ | $C_2H_4-COOC_2H_5$ | |
| 65 | 4-$OCHF_2$ | $CF_3$ | $CH_2CN$ | |
| 66 | 4-$OCHF_2$ | $CF_3$ | $CH_2COOCH_3$ | |
| 67 | 4-$OCHF_2$ | $CF_3$ | $CH_2CONH_2$ | |
| 68 | — | $CF_3$ | $CH_2-CH_2-N(CH_3)_2$ | 57–57° C./0.08 |
| 69 | — | $CF_3$ | $CH_2-CH_2-N\!\!\left\langle\begin{array}{c}\\\end{array}\right.$ (azetidinyl) | 87–90° C./0.09 |
| 70 | — | $CF_3$ | $CH_2-CH=CH_2$ | |
| 71 | — | $CF_3$ | $CH_2-CH=CH-CH_3$ | 55–57° C./0.1 |
| 72 | — | $CF_3$ | $CH(CH_3)CO-NH_2$ | $n_D^{24} = 1.4950$ |
| 73 | 4-F | $CF_3$ | $CH_2-CH=CH_2$ | 38–40° C./0.15 |
| 74 | 4-F | $CF_3$ | $CH_2-C\equiv CH$ | 55–56° C./0.9 |
| 75 | 3-$CF_3$ | $CF_3$ | $CH_2COOC_4H_9n$ | |
| 76 | 3-$CF_2$ | $CF_3$ | $CH_2COOCH(CH_3)C_2H_5$ | |
| 77 | 3-$CF_3$ | $CF_3$ | $CH_2COOCH_2CH(CH_3)_2$ | |
| 78 | 4-F | $CF_3$ | $CO-N(CH_3)CH_2-CN$ | |
| 79 | 4-Cl | $CF_3$ | $CO-NH-C_3H_7(n)$ | wax-like |
| 80 | 4-Cl | $CF_3$ | $CH_3$ | 80° C./19 |
| 81 | 4-Cl | $CF_3$ | $C_3H_7$ (n) | oil |
| 82 | 4-Cl | $CF_3$ | $CH_2-C\equiv CH$ | 55–59° C./0.2 |
| 83 | 4-Cl | $CF_3$ | $CH_2-CH=CH_2$ | 53–56° C./0.03 |
| 84 | 4-Cl | $CF_3$ | $CH_2-CO-NH_2$ | m.p. 63–65° C. |
| 85 | 4-Cl | $CF_3$ | $CH(CH_3)CO-NH_2$ | m.p. 79–81° C. |
| 86 | 4-Cl | $CF_3$ | $CH_2-CH\overset{\displaystyle\diagup O\diagdown}{\phantom{X}}CH_2$ | |
| 87 | 4-Cl | $CF_3$ | $CH_2-CH_2-N(CH_3)_2$ | |
| 88 | 4-Cl | $CF_3$ | $CH_2-CH_2-N\!\!\left\langle\begin{array}{c}\\\end{array}\right.$ (azetidinyl) | |
| 89 | 3-Cl | $CF_3$ | $CH_2COOC_6H_5$ | |
| 90 | 3-Cl | $CF_3$ | $CH_2COOC(CH_3)_2$ | |
| 91 | 3-Cl | $CF_3$ | $CH_2COOCH_2CH=CH_2$ | |
| 92 | 3,4-$Cl_2$ | $CF_3$ | $CH(CH_3)COONa$ | |
| 93 | 3,4-$Cl_2$ | $CF_2Cl$ | $CH(CH_3)COOK$ | |
| 94 | 3,4-$Cl_2$ | $CF_3$ | $CH(CH_3)CH=CHCOOCH_3$ | |
| 95 | 3-$NO_2$ | $CF_3$ | $CH_2CH=CHCOOCH_3$ | |
| 96 | 3-$NO_2$ | $CF_3$ | $CH(CH_3)CH=CHCOSCH_3$ | |
| 97 | 3-$NO_2$ | $CF_3$ | $CH_2COOCH_2CN$ | |
| 98 | 3-$NO_2$ | $CF_3$ | $CH_2COSCH_2CH=CH_2$ | |
| 99 | 3-$NO_2$ | $CF_3$ | $CH_2COOC_6H_5$ | |
| 100 | 3-$NO_2$ | $CF_3$ | $CH_2COSCH_2C\equiv CH$ | |
| 101 | 4-Cl | $CF_3$ | $CH_2-CH=CHCOSCH_3$ | |
| 102 | 4-Cl | $CF_3$ | $CH_2-CH=CHCOOCH_3$ | |
| 103 | 3,4-$Cl_2$ | $CF_3$ | $CH_2COOCH_2CH\equiv CH$ | |
| 104 | 3,4-$Cl_2$ | $CF_3$ | $CH_2CONHCHO$ | |
| 105 | 3,4-$Cl_2$ | $CF_3$ | $CH_2CONH-NH_2$ | |
| 106 | 3,4-$Cl_2$ | $CF_3$ | $CH(CH_3)NH-NH_2$ | |
| 107 | 3,4-$Cl_2$ | $CF_3$ | $CH_2-CSNHCH_2-CH=CH_2$ | |
| 108 | 4-$CH_3$ | $CF_3$ | $CH_2-CONHCONHC_6H_5$ | |
| 109 | 4-$CH_3$ | $CF_3$ | $CH_2-CONHCONHC_6H_4Cl(4)$ | |
| 110 | 4-$CH_3$ | $CF_3$ | $CH(CH_3)CONHCON(CH_3)_2$ | |
| 111 | 4-$CH_3$ | $CF_3$ | $CH_2CONHNH_2$ | |
| 112 | 4-$OCH_3$ | $CF_2Cl$ | $COCH_3$ | |
| 113 | 4-$OCH_3$ | $CF_2Cl$ | $COC_2H_5$ | |

-continued

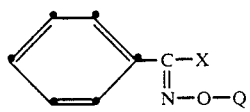

| No. | Phenyl substitution | X | Q | Physical data (°C.) |
|-----|---------------------|---|---|---------------------|
| 114 | 4-OCH₃ | CF₂Cl | COC₃H₇n | |
| 115 | 4-OCH₃ | CF₂Cl | COC₄H₉t | |
| 116 | 4-OCH₃ | CF₂Cl | COC₃H₇i | |
| 117 | 4-OCH₃ | CF₂Cl | COCH=C(CH₃)₂ | |
| 118 | 2-Cl, 4-CH₃ | CF₃ | COCH₂Cl | |
| 119 | 2-Cl, 4-CH₃ | CF₃ | COC(CH₃)₂CH₂Cl | |
| 120 | 2-Cl, 4-CH₃ | CF₃ | COCF₃ | |
| 121 | 2-Cl, 4-CH₃ | CF₃ | COC(Cl)=CCl₂ | |
| 122 | 2-Cl, 4-CH₃ | CF₃ | COCOOC₂H₅ | |
| 123 | 2-Cl, 4-CH₃ | CF₃ | COCOOC₂H₅ | |
| 124 | 2-Cl, 4-CH₃ | CF₃ | COCONH₂ | |
| 125 | 2-Cl, 4-CH₃ | CF₃ | COCH₂OCH₃ | |
| 126 | 2-Cl, 4-CH₃ | CF₃ | COCH₂OC₆H₅ | |
| 127 | 2-Cl, 4-CH₃ | CF₃ | COCH(CH₃)OC₆H₅ | |
| 128 | 2-Cl, 4-CH₃ | CF₃ | COCH(CH₃)OC₆H₄Cl(4) | |
| 129 | 2-Cl, 4-CH₃ | CF₃ | COCH(CH₃)OC₆H₄Cl(2) | |
| 130 | 2-Cl, 4-CH₃ | CF₃ | COCH₂OC₆H₃Cl₂(2,4) | |
| 131 | 2-Cl, 4-CH₃ | CF₃ | COCH(CH₃)C₆H₃Cl(2)CH₃(4) | |
| 132 | 2-Cl, 4-CH₃ | CF₃ | COCH₂SC₆H₅ | |
| 133 | 2-Cl, 4-CH₃ | CF₃ | COCH(CH₃)SC₆H₅Cl(4) | |
| 134 | 2-Cl, 4-CH₃ | CF₃ | COCH₃C₆H₅ | |
| 135 | 2-Cl, 4-CH₃ | CF₃ | COCH₂C₆H₄Cl | |
| 136 | 2-Cl, 4-CH₃ | CF₃ | COCH(C₃H₇i)C₆H₅ | |
| 137 | 2-Cl, 4-CH₃ | CF₃ | COCH(C₃H₇i)C₃H₄Cl(4) | |
| 138 | 2-Cl, 4-CH₃ | CF₃ | CO-cyclopropyl | |
| 139 | 2-Cl, 4-CH₃ | CF₃ | CO-1-methylcyclopropyl | |
| 140 | 2-Cl, 4-CH₃ | CF₃ | CO-2,2-dimethylcyclopropyl | |
| 141 | 2-Cl, 4-CH₃ | CF₃ | CO-2,2dichlorocyclopropyl | |
| 142 | 2-Cl, 4-CH₃ | CF₃ | CO-cyclopentyl | |
| 143 | 2-Cl, 4-CH₃ | CF₃ | CO-cyclohexyl | |
| 144 | 2-Br | CF₂Cl | COC₆H₅ | |
| 145 | 2-Br | CF₂Cl | COC₆H₄(CH₃)(2) | |
| 146 | 2-Br | CF₂Cl | COC₆H₄(CH₃)(3) | |
| 147 | 2-Br | CF₂Cl | COC₆H₄Cl(4) | |
| 148 | 2-Br | CF₂Cl | COC₆H₄(CF₃)(3) | |
| 149 | 2-Br | CF₂Cl | COC₆H₄(CF₃)(2) | |
| 150 | 2-Br | CF₂Cl | COC₆H₄(OCF₃)(4) | |
| 151 | 2-Br | CF₂Cl | COC₆H₄(NO₂)(2) | |
| 152 | 2-Br | CF₂Cl | COC₆H₄Cl(3) | |
| 153 | 2-Br | CF₂Cl | COC₆H₄(OCH₃)(4) | |
| 154 | 2-Br | CF₂Cl | COC₆H₄(OCOCH₃)(2) | |
| 155 | 2-Br | CF₂Cl | COC₆H₃(Cl₂)(3,4) | |
| 156 | 2-Br | CF₂Cl | COC₆H₃(NO₂)(3)(CH₃)(4) | |
| 157 | 3-NO₂ | C₂F₅ | nicotinoyl | |
| 158 | 3-NO₂ | C₂F₅ | isonicotinoyl | |
| 159 | 3-NO₂ | C₂F₅ | 2,6-dichloroisonicotinoyl | |
| 160 | 3-NO₂ | C₂F₅ | 3-furoyl | |
| 161 | 3-NO₂ | C₂F₅ | thienyl-2-carbonyl | |
| 162 | 3-NO₂ | C₂F₃ | 4-methyl-1,2,3-thiadiazole-5-carbonyl | |
| 163 | 3-NO₂ | C₂F₃ | 3,5-dimethyl-1,2-oxazolyl-2-carbonyl | |
| 164 | 3-NO₂ | C₂F₃ | 2,5-dimethylfuroyl-2-carbonyl | |
| 165 | 3-NO₂ | C₂F₃ | 2-methyl-4,5-dihydropyranyl-3-carbonyl | |
| 166 | 3-NO₂ | C₂F₃ | 3-methyl-2,3-dihydro-1,4-thioxinyl-2-carbonyl | |
| 167 | 3-NO₂ | C₂F₃ | 3-methyl-2,3-dihydro-1-oxo-1,4-thioxinyl-2-carbonyl | |
| 168 | 3-NO₂ | C₂F₃ | 2,4-dimethyl-1,4-thiazolyl-2-carbonyl | |
| 169 | 2,4-Br₂ | CF₃ | 1,4-thiazolyl-2-carbonyl | |
| 170 | 2,4-Br₂ | CF₃ | 1,4-dichloropyrimidinyl-5-carbonyl | |
| 171 | 2,4-Br₂ | CF₃ | 3-bromo-2-furoyl | |
| 172 | 2,4-Br₂ | CF₃ | CH₂C₆H₅ | |
| 173 | 2-Cl, 4-Br | CF₃ | CH₂C₆H₄Cl(4) | |
| 174 | 2-Cl, 4-Br | CF₃ | CH₂C₆H₃Cl₂(2,4) | |
| 175 | 2-Cl, 4-Br | CF₃ | CH₂C₆H₄Br(4) | |
| 176 | 2-Cl, 4-Br | CF₃ | CH₂C₆H₄(CN)(4) | |
| 177 | 2-Cl, 4-Br | CF₃ | CH₂C₆H₄(CH₃)(4) | |
| 178 | 2-Cl, 4-Br | CF₃ | CH₂C₆H₄(C₃H₇i)(4) | |
| 179 | 2-Cl, 4-Br | CF₃ | CH₂C₆H₄F(2) | |
| 180 | 2-Cl, 4-Br | CF₃ | CH₂C₆H₃F₂(2,6) | |
| 181 | 2-Cl, 4-Br | CF₃ | CH₂C₆H₄(NO₂)(4) | |
| 182 | 2-Cl, 4-Br | CF₃ | CH₂C₆H₄(OCH₃)(3) | |
| 183 | 2-Cl, 4-Br | CF₃ | C₂H₄C₆H₅ | |
| 184 | 2-Cl, 4-Br | CF₃ | CH₂C₆H₅(C₆H₅)(4) | |
| 185 | 4-OCH₃ | C₃H₄F₃ | CONHCH₃ | |
| 186 | 4-OCH₃ | C₃H₄F₃ | CONH₂ | |
| 187 | 4-OCH₃ | C₃H₄F₃ | CONHC₂H₅ | |
| 188 | 4-OCH₃ | C₃H₄F₃ | CONHC₆H₅ | |

-continued

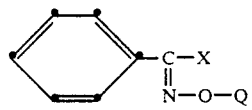

| No. | Phenyl substitution | X | Q | Physical data (°C.) |
|---|---|---|---|---|
| 189 | 4-OCH$_3$ | C$_3$H$_4$F$_3$ | CONHC$_6$H$_3$(CH$_3$)$_2$(2,6) | |
| 190 | 4-OCH$_3$ | C$_3$H$_4$F$_3$ | CONH-cyclohexyl | |
| 191 | 4-OCH$_3$ | C$_3$H$_4$F$_3$ | CONHC$_3$H$_7$n | |
| 192 | 4-OCH$_3$ | C$_3$H$_4$F$_3$ | CONHC$_3$H$_7$i | |
| 193 | 4-OCH$_3$ | C$_3$H$_4$F$_3$ | CONHC$_6$H$_4$Cl(4) | |
| 194 | 4-OCH$_3$ | C$_3$H$_4$F$_3$ | CONHC$_4$H$_9$t | |
| 195 | 4-OCH$_3$ | C$_3$H$_4$F$_3$ | CONHC$_6$H$_4$(OC$_2$H$_5$)(4) | |
| 196 | 4-OCF$_3$ | CF$_3$ | CONHC$_6$H$_4$(CF$_3$)(3) | |
| 197 | 4-OCF$_3$ | CF$_3$ | CSNHC$_6$H$_5$ | |
| 198 | 4-OCF$_3$ | CF$_3$ | CSNHC$_6$H$_4$(CH$_3$)(4) | |
| 199 | 4-OCF$_3$ | CF$_3$ | SO$_2$CH$_3$ | |
| 200 | 4-OCF$_3$ | CF$_3$ | SO$_2$CH$_2$Cl | |
| 201 | 4-OCF$_3$ | CF$_3$ | SO$_2$C$_6$H$_5$ | |
| 202 | 4-OCF$_3$ | CF$_3$ | SO$_2$N(CH$_3$)$_2$ | |
| 203 | 4-OCF$_3$ | CF$_3$ | SO$_2$C$_6$H$_4$Cl(4) | |
| 204 | 4-OCF$_3$ | CF$_3$ | SO$_2$C$_6$H$_4$(CH$_3$)(4) | |
| 205 | 4-OCF$_3$ | CF$_3$ | piperidinosulfonyl | |
| 206 | 4-OCF$_3$ | CF$_3$ | morpholinosulfonyl | |
| 207 | 4-OCF$_3$ | CF$_3$ | piperidylsulfonyl | |
| 208 | 4-Cl | CF$_2$Cl | succinimidomethyl | |
| 209 | 4-Cl | CF$_3$ | 2,3-dimethylmaleylimidomethyl | |
| 210 | — | CF$_3$ | succinimidomethyl | |
| 211 | — | CF$_3$ | 2,3-dimethylmaleylimidomethyl | |
| 212 | 4-Cl | CF$_3$ | maleylimidomethyl | |
| 213 | — | CF$_3$ | maleylimidomethyl | |
| 214 | 4-Cl | CF$_3$ | phthalimidomethyl | |
| 215 | — | CF$_3$ | phthalimidomethyl | |
| 216 | 4-Cl | CF$_3$ | 3,4,5,6-tetrahydrophthalimidomethyl | |
| 217 | 4-Cl | CF$_3$ | 1,2,3,4-tetrahydrophthalimidomethyl | |
| 218 | — | CF$_3$ | 3,4,5,6-tetrahydrophthalimidomethyl | |
| 219 | — | CF$_3$ | 1,2,3,4-tetrahydrophthalimidomethyl | |
| 220 | 4-Cl | CF$_3$ | SO$_2$N(C$_3$H$_7$-i)CH$_2$OCH$_3$ | |
| 221 | 4-Cl | CF$_3$ | SO$_2$N(CH$_3$)CH$_2$OCH$_3$ | |
| 222 | 4-Cl | CF$_3$ | SO$_2$N(C$_2$N(C$_2$H$_5$)CH$_2$OCH$_3$ | |
| 223 | 4-Cl | CF$_3$ | SO$_2$CCl$_3$ | |
| 224 | 4-Cl | CHF$_2$ | CH$_2$CN | |
| 225 | 4-Cl | CHF$_2$ | CH(CH$_3$)CN | |
| 226 | 4-Cl | CHF$_2$ | CH$_2$CONH$_2$ | |
| 227 | 4-Cl | CHF$_2$ | CH(CH$_3$)CONH$_2$ | |
| 228 | 4-Cl | CF$_3$ | 2,4,6-trichloropyridino | |
| 229 | 4-Cl | CHF$_2$ | 2,4,6-trichloropyridino | |
| 230 | 4-Cl | CF$_3$ | 2,4,6-tribromopyridino | |
| 231 | 4-Cl | CF$_3$ | 3,5-dichloropyridino | |
| 232 | 4-Cl | CF$_3$ | 3,5-dichloropyridino | |
| 233 | 4-Cl | CF$_3$ | 5-chloro-3-trifluoromethylpyridino | |
| 234 | 4-Cl | CHF$_2$ | 5-chloro-3-trifluoromethylpyridino | |
| 235 | 4-OCH$_3$ | CF$_3$ | CH$_2$CN | |
| 236 | 4-OCH$_3$ | CF$_3$ | CH$_2$CONH$_2$ | |
| 237 | — | CF$_3$ | 2,4,6-trichloropyridino | |
| 238 | — | CF$_3$ | 3,5-dichloropyridino | |
| 239 | — | CF$_3$ | 5-chloro-3-trifluoromethylpyridino | |
| 240 | — | CF$_3$ | SO$_2$N(CH$_3$)CH$_2$OCH$_3$ | |
| 241 | — | CF$_3$ | SO$_2$N(C$_2$H$_5$)CH$_2$OCH$_3$ | |
| 242 | — | CF$_3$ | SO$_2$N(C$_3$H$_7$i)CH$_2$OCH$_3$ | |
| 243 | — | CF$_3$ | SO$_2$CCl$_3$ | |
| 244 | — | CHF$_2$ | CH$_2$CN | |
| 245 | — | CHF$_2$ | CH$_2$OCH$_3$ | |
| 246 | 4-Cl | CF$_3$ | CH$_2$—C≡CI | |
| 247 | — | CF$_3$ | CH$_2$—C≡CI | |
| 248 | — | CF$_3$ | C$_2$H$_4$OH | |
| 249 | 4-Cl | CF$_3$ | CH$_2$—COOCH$_3$ | 78–80° C./0.06 |
| 250 | — | CF$_3$ | C$_2$H$_4$OH | |
| 251 | 4-Cl | CF$_3$ | C$_2$H$_4$OH | |
| 252 | — | CF$_3$ | C$_2$H$_4$OCOCH$_3$ | |
| 253 | 4-Cl | CF$_3$ | C$_2$H$_4$OCOCH$_3$ | |
| 254 | — | CF$_3$ | C$_2$H$_4$OCONHCH$_3$ | |
| 255 | 4-Cl | CF$_3$ | C$_2$H$_4$OCONHCH$_3$ | |
| 256 | — | CF$_3$ | C$_2$H$_4$OCH$_2$CH=CH$_2$ | |
| 257 | 4-Cl | CF$_3$ | C$_2$H$_4$OCH$_2$CH=CH$_2$ | |
| 258 | 3-CF$_3$ | CF$_3$ | CH$_2$—CH——CH$_2$ \ / CH$_2$ | b.p. 57–57° C./0.08 mbar |

-continued

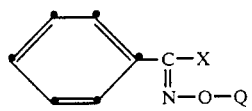

| No. | Phenyl substitution | X | Q | Physical data (°C.) |
|-----|---------------------|---|---|---------------------|
| 259 | 3-$CF_3$ | $CF_3$ | $CH_2$—$CONH_2$ | wax-like |
| 260 | — | $C_2F_5$ | $CH_2$—$CONH_2$ | b.p. 90–100°/0.05 mbar |
| 261 | 3-$CF_3$ | $CF_3$ | $CH(CH_3)CONH_2$ | b.p. 102–111° 0.08 mbar |
| 262 | 4-F | $CF_3$ | $CH_2C_6H_4F(2)$ | b.p. 81–83°/0.03 mbar |
| 263 | 4-Cl | $CF_3$ | $CH_2C_6H_4F(2)$ | b.p. 95–96°/0.08 mbar |
| 264 | 4-F | $CF_3$ | $CH_2C_6H_4F(4)$ | b.p. 76–77°/0.04 mbar |
| 265 | 4-Cl | $CF_3$ | $CH_2C_6H_4F(4)$ | b.p. 95–97°/0.05 mbar |
| 266 | 4-$CH_3$ | $CF_3$ | $CH_2CN$ | b.p. 83–84°/0.1 mbar |
| 267 | 4-F | $CF_3$ | $CH_2COCH(CH_3)_2$ | |
| 268 | 4-Cl | $CF_3$ | $CH$—$CH_2$ with $CH_2$ (cyclopropyl) | |
| 269 | 4-Cl | $CF_3$ | $CH_2$—CO—$NHCH_3$ | |
| 270 | 4-Cl | $CF_3$ | $CH_2CON(CH_3)_2$ | |
| 271 | 4-Cl | $CF_3$ | $CH_2CONHC_2H_5$ | |
| 272 | 4-Cl | $CF_3$ | $CH_2COOC_2H_5$ | |
| 273 | 4-Cl | $CF_3$ | $CH(CH_3)COOC_2H_5$ | |
| 274 | 2-Cl | $CF_3$ | $CH_2CONH_2$ | m.p. = 70–73° C. |
| 275 | 2-Cl | $CF_3$ | $CH(CH_3)CONH_2$ | b.p. = 121–123° C./0.12 |
| 276 | 2-Cl | $CF_3$ | $CH_2COOC_2H_5$ | |
| 277 | 2-Cl | $CF_3$ | $CH(CH_3)COOC_2H_5$ | |
| 278 | 4-Cl | $CF_3$ | $CH(CH_3)COOC_2H_5$ | |
| 279 | 4-Cl | $CF_3$ | $CH(CH_3)COOC_3H_7n$ | |
| 280 | 4-Cl | $CF_3$ | $CH(CH_3)COOCH_2CH=CH_2$ | |
| 281 | 4-Cl | $CF_3$ | $CH_2CSNH_2$ | |
| 282 | 4-Cl | $CF_3$ | $CH(CH_3)CSNH_2$ | |
| 283 | 4-$CH_3$ | $CF_3$ | $CH_2CONH_2$ | m.p. = 92–94° C. |
| 284 | 4-$CH_3$ | $CF_3$ | $CH(CH_3)CONH_2$ | m.p. = 76–77° C. |
| 285 | 3,4($CH_3)_2$ | $CF_3$ | $CH_2CONH_2$ | |
| 286 | 3,4($CH_3)_2$ | $CF_3$ | $CH(CH_3)CONH_2$ | |
| 287 | — | $C_2H_5$ | $CH_2CONH_2$ | |
| 288 | — | $C_2H_5$ | $CH(CH_3)CONH_2$ | |
| 289 | 4-$CH_3$ | $CF_3$ | $CH_2COOCH_3$ | |
| 290 | 4-$CH_3$ | $CF_3$ | $CH_2COOC_3H_7n$ | |
| 291 | 4-$CH_3$ | $CF_3$ | $CH(CH_3)COOC_2H_5$ | |
| 292 | 4-Cl | $CF_3$ | $CH_2COSC_2H_5$ | |
| 293 | 4-Cl | $CF_3$ | $CH_2COOC_2H_4OCH_3$ | |
| 294 | 4-Cl | $CF_3$ | $CH_2COOC_2H_4Cl$ | |
| 295 | 4-$OCH_3$ | $CF_3$ | $CH_2CONH_2$ | |
| 296 | 3-$NO_2$ | $CF_3$ | $CH_2CONH_2$ | |
| 297 | 4-Cl | $CHF_2$ | $CH_2CONH_2$ | |
| 298 | 4-Cl | $CHF_2$ | $CH(CH_3)CONH_2$ | |
| 300 | 4-Cl | $CHF_2$ | $CH(CH_3)COOC_2H_5$ | |
| 301 | 4-Cl | $CF_3$ | $SO_2CF_3$ | |
| 302 | 4-Cl | $CF_3$ | $SO_2CHCl$ | |
| 303 | 4-Cl | $CF_3$ | $CH_2$—$COOC_3H_7$iso | 90–91° C./0.09 |
| 304 | 4-Cl | $CF_3$ | $CH_2CONHNH_2$ | |
| 305 | 4-Cl | $CF_3$ | $CH(CH_3)CONHNH_2$ | |
| 306 | 4-Cl | $CHF_2$ | $CH_2$—CH—$CH_2$ with $CH_2$ (cyclopropyl) | |
| 307 | 4-Cl | $CF_3$ | $C_2H_4COOC_2H_5$ | |
| 308 | 4-Cl | $CF_3$ | $CH(C_2H_5)CONH_2$ | |
| 309 | 4-Cl | $CF_3$ | $CH_2COOCH_2CF_3$ | 77–78° C./0.06 |
| 310 | 4-F | $CF_3$ | $CH_2COOCH_2CF_3$ | |
| 311 | 4-$CH_3$ | $CF_3$ | $CH_2COOCH_2CF_3$ | |
| 312 | 4-Cl | $CF_3$ | 2-tetrahydrofurfurylmethyl | 127–129°/0.03 (example 2) |
| 313 | 4-F | $CF_3$ | $CH_2COOCH_3$ | 70–72°/0.06 |
| 314 | 4-F | $CF_3$ | $CH_2COOC_2H_5$ | 73–75°/0.05 |
| 315 | 4-F | $CF_3$ | $CH_2COOCH(CH_3)_2$ | 68–70°/0.08 |
| 316 | 4-$OCH_3$ | $CF_3$ | $CH_2COOCH(CH_3)_2$ | |
| 317 | 4-$CH_3$ | $CF_3$ | 2-tetrahydrofurfurylmethyl | |
| 318 | 3-$CF_3$ | $CF_3$ | 2-tetrahydrofurfurylmethyl | |
| 319 | 4-$OCH_3$ | $CF_3$ | 2-tetrahydrofurfurylmethyl | |
| 320 | 4F | $CF_3$ | $CH_2COOCH_2CH(CH_3)_2$ | |
| 321 | 3-$CF_3$ | $CF_3$ | benzyl | 123–125°/0.07 |
| 322 | 4-Cl | $CF_3$ | $CH_2COOCH_2CH(CH_3)_2$ | 88–89°/0.03 |
| 323 | 4-Cl | $CF_3$ | $CH_2COOCH(CH_3)C_2H_5$ | 104–105°/0.1 |
| 324 | 4-Cl | $CF_3$ | $CH(CH_3)COOCH(CH_3)C_2H_5$ | |
| 325 | 4-Cl | $CF_3$ | $CH_2COOC_4H_9n$ | |

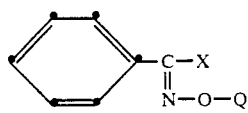

| No. | Phenyl substitution | X | Q | Physical data (°C.) |
|---|---|---|---|---|
| 326 | 4-Cl | $CF_3$ | $CH_2COOC(CH_3)_3$ | |
| 327 | 4-Cl | $CF_3$ | $CH_2COOC_5H_{11}iso$ | |
| 328 | 4-Cl | $CF_3$ | $CH(CH_3)COOCH_2CH(CH_3)_2$ | |
| 329 | 4-$OC_2H_5$ | $CF_3$ | $CH_2COOCH(CH_3)_2$ | |
| 330 | 3-$CF_3$ | $CF_3$ | $CH_2COOCH_3$ | |
| 331 | 3-$CF_3$ | $CF_3$ | $CH_2COOC_2H_5$ | 63–65°/0.07 (exmple 3) |
| 332 | 3-$CF_3$ | $CF_3$ | $CH_2COOCH(CH_3)_2$ | 161–162°/0.06 |

EXAMPLE 4

Formulation examples for compounds of formula I or mixtures thereof with herbicides (percentages are by weight)

| (a) Wettable powders | (a) | (b) | (c) |
|---|---|---|---|
| Compound of formula I or mixture thereof with a herbicide | 20% | 60% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| Compound of formula I or mixture thereof with a herbicide | 10% | 1% |
| octylphenol polyethylene glycol ether (4–5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I or mixture thereof with a herbicide | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I or mixture thereof with a herbicide | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I or mixture thereof with a herbicide | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I or mixture thereof with a herbicide | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I or mixture thereof with a herbicide | 5% |
| isopropylamine | 1% |
| octylphenol polyethylene glycol ether (78 moles of ethylene oxide) | 3% |
| water | 91% |

BIOLOGICAL EXAMPLES

The ability of the compounds of formula I to protect cultivated plants from the phytotoxic effects of potent herbicides is illustrated in the following Examples In the test procedures the compounds of formula I are referred to as antidotes (safeners).

EXAMPLE 5

Test with antidote and herbicide in sorghum. Preemergence application of herbicide and antidote as tank mixture.

Plastic containers measuring 25 cm × 17 cm × 12 cm are filled with sandy loam and Funk G 522 sorghum seeds are sown therein. The seeds are then lightly covered with a layer of soil onto which is sprayed a dilute aqueous solution containing the herbicide and the antidote in the desired ratio. The condition of the plants is assessed 30 days later.

The protective action is expressed in percent and indicates the degree to which the antidote (safener) is able to reduce the phytotoxic action of the herbicide. A significant effect is achieved in the phytoxicity if the range of severe to average damage can be reduced to that of slight, reversible damage or to complete tolerance.

The results are as follows:

| Herbicide: 2-chloro-6'-ethyl-N-("-methoxy-1"'-methylethyl)-acet-o-toluidide ("metolachlor") | | |
|---|---|---|
| Antidote No. | Herbicide kg/ha | Relative protective action in % |
| 4 | 1.5  1.5 | 25 |
| 5 | 1.5  1.5 | 13 |
| 8 | 1.5  1.5 | 25 |
| 14 | 1.5  1.5 | 63 |
| 71 | 1.5  1.5 | 13 |
| 81 | 1.5  1.5 | 38 |
| 83 | 1.5  1.5 | 25 |
| 84 | 1.5  1.5 | 63 |
| 85 | 1.5  1.5 | 13 |
| 259 | 1.5  1.5 | 50 |
| 261 | 1.5  1.5 | 38 |
| 264 | 1.5  1.5 | 38 |
| 267 | 1.5  1.5 | 25 |
| 312 | 1.5  1.5 | 63 |
| 313 | 1.5  1.5 | 63 |
| 314 | 1.5  1.5 | 63 |
| 315 | 1.5  1.5 | 50 |
| 322 | 1.5  1.5 | 63 |
| 323 | 1.5  1.5 | 50 |
| 324 | 1.5  1.5 | 50 |
| 329 | 1.5  1.5 | 50 |
| 331 | 1.5  1.5 | 50 |
| 332 | 1.5  1.5 | 75 |
| 333 | 1.5  1.5 | 75 |

EXAMPLE 6

Preemergence test with antidote and herbicide in sorghum. Application of the antidote by seed dressing.

Funk G 522 sorghum seeds are mixed with the antidote in a glass flask. Seeds and compound are thoroughly mixed by shaking and rotating the flask. Finally the dressed seeds are sown in flower pots (diameter at the top 11 cm) filled with sandy loam. The seeds are covered lightly with soil onto which an aqueous emulsion of the herbicide is sprayed in the desired concentration. The condition of the plants is assessed 8 days after the treatment with the herbicide and the relative protective action is expressed in percent. The results are as follows:

| Herbicide: 2-chloro-6'-ethyl-N-(2"-methoxy-1"'-methylethyl)-acet-o-toluide ("metolachlor") | | |
|---|---|---|
| Antidote No. | g/kg seeds | Herbicide kg/ha | Relative protective action in % |
| 5 | 2 | 4 | 88 |
| 5 | 1 | 4 | 50 |
| 5 | 0.5 | 4 | 25 |
| 5 | 2 | 2 | 63 |
| 5 | 1 | 2 | 50 |
| 5 | 0.5 | 2 | 50 |
| 5 | 2 | 1 | 75 |
| 5 | 1 | 1 | 38 |
| 5 | 0.5 | 1 | 38 |
| 13 | 2 | 4 | 50 |
| 13 | 1 | 4 | 50 |
| 13 | 0.5 | 4 | 25 |
| 13 | 2 | 2 | 75 |
| 13 | 1 | 2 | 63 |
| 13 | 0.5 | 2 | 25 |
| 13 | 2 | 1 | 75 |
| 13 | 1 | 1 | 63 |
| 13 | 0.5 | 1 | 38 |
| 84 | 2 | 4 | 38 |
| 84 | 1 | 4 | 50 |
| 84 | 0.5 | 4 | 50 |
| 84 | 2 | 2 | 38 |
| 84 | 1 | 2 | 50 |
| 84 | 0.5 | 2 | 50 |
| 84 | 2 | 1 | 38 |
| 84 | 1 | 1 | 50 |
| 84 | 1 | 1 | 50 |
| 312 | 2 | 2 | 63 |
| 313 | 2 | 2 | 63 |
| 314 | 2 | 2 | 63 |
| 315 | 2 | 2 | 50 |
| 322 | 2 | 2 | 63 |
| 323 | 2 | 2 | 50 |
| 324 | 2 | 2 | 50 |
| 329 | 2 | 2 | 50 |
| 331 | 2 | 2 | 75 |
| 333 | 2 | 2 | 75 |

EXAMPLE 7

Test with antidote and herbicide in soybeans. Preemergence application of herbicide and antidote as tank mixture.

Flower pots (diameter at the top 6 cm) are filled with sandy loam and "Hark" soybean seeds are sown therein. The seeds are covered and a dilute solution of the compound for testing as safener, together with the herbicide, is sprayed as tank mixture onto the surface of the soil. The protective action is evaluated (in %) 21 days after application. The result is as follows:

| Herbicide: 4-amino-3-methylthio-6-tert-butyl-1,2,4-triazin-5-one ("metribuzin") | | |
|---|---|---|
| Antidote No. | Herbicide kg/ha | Relative protective action in % |
| 1 | 1.5  0.75 | 50 |

EXAMPLE 8

Test with antidote and herbicide in wheat. Preemergence application of herbicide and antidote as tank mixture.

"Farnese" wheat seeds are sown in plastic pots (diameter at the top 11 cm) containing 0.5 liter of earth in a greenhouse. The seeds are covered and the compound for testing as safener is applied, together with the herbicide, as tank mixture. The protective action of the safener is evaluated (in %) 24 days after application. The results are reported below:

| Herbicide: Propynyl α-[4-(2,4-dichloropyridyl-2-oxy) phenoxy]-propionate | | | |
|---|---|---|---|
| Antidote No. | kg/ha | Herbicide kg/ha | Relative protective action in % |
| 5 | 1.5 | 0.75 | 38 |
| 8 | 1.5 | 0.75 | 25 |
| 14 | 1.5 | 0.75 | 38 |
| 72 | 1.5 | 0.75 | 25 |
| 79 | 1.5 | 0.75 | 38 |
| 81 | 1.5 | 0.75 | 25 |
| 84 | 1.5 | 0.75 | 38 |
| 85 | 1.5 | 0.75 | 38 |

EXAMPLE 9

Test with antidote and herbicide in maize. Application of the antidote by seed dressing.

LG 5 maize seeds are mixed together with the safener for testing in a glass beaker. Seeds and compound are thoroughly mixed by shaking and rotation. Plastic pots (diameter at the top 11 cm) are filled with soil and the dressed seeds are sown therein. The seeds are covered and then some of the herbicides are applied preemergence in substantial overdose. The protective action of the safener is determined in percent 18 days after application of the herbicide. The plants treated with herbicide alone and the completely untreated controls are used for reference purposes. The results are as follows:

| Herbicide: 2-chloro-6'-ethyl-N-(2"-methoxy-1"-methylethyl) acet-o-toluide ("metolachlor") | | | |
|---|---|---|---|
| Antidote No. | g/kg seeds | Herbicide kg/ha | Relative protective action in % |
| 84 | 2 | 6 | 75 |
| 84 | 1 | 6 | 75 |
| 84 | 1.5 | 6 | 75 |

| Herbicide: S-ethyl-dipropylthiocarbamate ("EPTC") | | | |
|---|---|---|---|
| Antidote No. | g/kg seeds | Herbicide kg/ha | Relative protective action in % |
| 84 | 2 | 6 | 50 |
| 84 | 1 | 6 | 63 |
| 84 | 0.5 | 6 | 38 |
| 84 | 2 | 4 | 63 |
| 84 | 1 | 4 | 63 |
| 84 | 0.5 | 4 | 38 |

| Herbicide: N-isopentyl-3,4-dimethyl-2,6-dinitroaniline ("penoxalin") | | | |
|---|---|---|---|
| Antidote No. | g/kg seeds | Herbicide kg/ha | Relative protective action in % |
| 84 | 2 | 4 | 50 |
| 84 | 1 | 4 | 50 |
| 84 | 0.5 | 4 | 25 |
| 84 | 2 | 2 | 25 |
| 84 | 2 | 2 | 25 |
| 84 | 0.5 | 2 | 38 |

EXAMPLE 10

Test with antidote and herbicide in maize. Preemergence application of antidote and herbicide as tank mixture.

Plastic containers measuring 25 cm × 17 cm × 12 cm are filled with sandy loam and LG 5 maize seeds are sown therein. The seeds are covered and a dilute solution of the safener for testing, together with an overdose of herbicide, is applied as tank mixture to the surface of the soil. The protective action of the safener is evaluated in percent 21 days after application. The plants treated with herbicide alone as well as the completely untreated controls are used for reference purposes. The results are as follows:

| Herbicide: 2-chloro-6'-ethyl-N-(2"-methoxy-1"-methylethyl) acet-o-toluide ("metolachlor"). | | | |
|---|---|---|---|
| Antidote No. | kg/ha | Herbicide kg/ha | Relative protective action in % |
| 84 | 3 | 6 | 50 |
| 84 | 1.5 | 6 | 38 |
| 84 | 0.75 | 6 | 25 |

EXAMPLE 11

Test with antidote and herbicide in dry sown rice. Preemergence application of herbicide and antidote as tank mixture.

Rice seeds are sown in containers measuring 47 cm × 29 cm × 24 cm, covered, and the soil is lightly pressed firm. Then a dilute solution of the antidote for testing, together with the herbicide, is sprayed onto the surface of the soil as tank mixture. The protective action of the herbicide is evaluated in percent 24 days after sowing. The plants treated with herbicide alone and the completely untreated controls are used for reference purposes. The results are reported below.

| Herbicide: 2-chloro-6'-ethyl-N-(2"-methoxy-1"-methylethyl) acet-o-toluidide ("metolachlor") | | | |
|---|---|---|---|
| Antidote No. | kg/ha | Herbicide kg/ha | Relative protective action in % |
| 260 | 1.5 | 0.25 | 25 |

EXAMPLE 12

Test with antidote and herbicide in dry sown and subsequently flooded rice. Preemergence application of herbicide and antidote as tank mixture.

Rice seeds of the IR-36 variety are sown in containers measuring 47×29×24 cm, covered, and the soil is lightly pressed firm. The compound for testing as antidote together with the herbicide are then sprayed as tank mixture. About 20 days after sowing (when the rice plants are in the 3-leaf stage), the surface of the soil is covered with water to a height of 4 cm. The protective action of the antidote is evaluated 30 days after application. Plants treated with herbicide alone and completely untreated controls are used for reference purposes. The results are set forth below.

| Herbicide: 2-chloro-6'-ethyl-N-(2''-methoxy-1''-methylethyl) acet-o-toluidide ("metolachlor") | | |
|---|---|---|
| Antidote No. | Herbicide kg/ha | Relative protective action in % |
| 260 | 1.5 / 0.25 | 25 |

EXAMPLE 13

Test with antidote and herbicide in rice sown in water.

Application of the antidote during immersion of the rice seeds. Rice seeds are immersed for 48 hours in 10, 100 and 1000 ppm solutions of the compound for testing as safener. The seeds are then allowed to dry for about 2 hours until they are no longer tacky. Plastic containers measuring 25 cm×17 cm×12 cm are filled with sandy loam to 2 cm below the edge. The pretreated seeds are sown on the surface of the soil in the containers and only lightly covered. The soil is kept in a moist (non-marshy) state. Then a dilute solution of the herbicide is sprayed onto the surface of the soil. The water level is then gradually raised in accordance with growth of the rice plants. The protective action of the safener is evaluated (in %) 18 days after application. The plants treated with herbicide alone and the completely untreated controls are used for reference purposes. The results are as follows:

| Herbicide: 2-chloro-2',6'-diethyl-N-(2''-propylethyl)acetanilide ("pretilachlor"). | | |
|---|---|---|
| Antidote No. | ppm | Herbicide kg/ha | Relative protective action in % |
| 18 | 100 | 0.25 | 25 |
| 260 | 100 | 0.25 | 50 |

What is claimed is:

1. An oxime of the formula

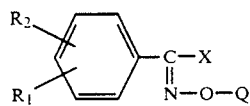

wherein

X is trifluoromethyl or pentafluoroethyl;

$R_1$ is hydrogen, halogen, $C_1$-$C_4$-alkyl, $C_1$-$C_4$-haloalkyl, $C_1$-$C_4$-alkoxy, $C_1$-$C_4$-haloalkoxy or nitro;

$R_2$ is hydrogen, halogen, $C_1$-$C_4$-alkyl or $C_1$-$C_4$-alkoxy;

Q is $C_1$-$C_8$-alkyl unsubstituted or substituted by halogen; phenyl wherein the phenyl ring is unsubstituted or substituted by halogen, $C_1$-$C_4$-alkyl, $C_1$-$C_4$-haloalkyl, $C_1$-$C_4$-alkoxy, $C_1$-$C_4$-haloalkoxy or nitro; cyclopropylmethyl; benzyl; fluorobenzyl; $C_3$-$C_6$-cycloalkyl; $C_3$-$C_6$-alkenyl; $C_3$-$C_6$-haloalkenyl; $C_3$-$C_6$-alkynyl; $C_1$-$C_8$-alkylcarbonyl; $C_1$-$C_8$-haloalkylcarbonyl; $C_3$-$C_6$-alkenylcarbonyl; $C_3$-$C_6$-haloalkenylcarbonyl; $C_3$-$C_6$-alkynylcarbonyl; $C_3$-$C_8$-cycloalkylcarbonyl; or benzoyl, the phenyl ring of which is unsubstituted or substituted by halogen, $C_1$-$C_4$-alkyl, $C_1$-$C_4$-alkyl, $C_1$-$C_4$-haloalkyl, $C_1$-$C_4$-alkoxy, $C_1$-$C_4$ haloalkoxy or nitro.

2. An oxime ether according to claim 1 of the formula Id

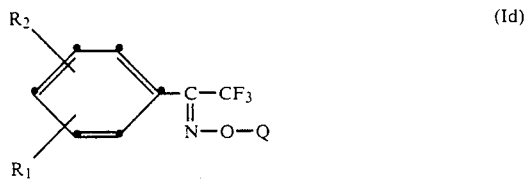

wherein $R_1$ and $R_2$ are as defined in claim 1 and B is $C_1$-$C_4$alkyl or $C_3$-$C_6$cycloalkyl.

3. 1-Phenyl-1-methoximino-2,2,2-trifluoroethane according to claim 1.

4. 1-(3-Trifluormethylphenyl)-1-cyclopropylmethoximino-2,2,2-trifluoroethane according to claim 1.

5. 1-(4-Chlorophenyl)-1-n-propoximino-2,2,2-trifluorethane according to claim 1.

6. An oxime ether according to claim 1 of the formula

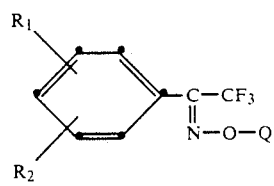

wherein $R_1$ and $R_2$ are as given in claim 1 and Q represents a $C_3$-$C_6$-alkenyl which is unsubstituted or substituted by halogen.

7. 1-(4-Chlorophenyl)-1-allyloximino-2,2,2-trifluoroethane according to claim 1.

8. 1-Phenyl-1-(but-2-enyloximino)-2,2,2-trifluoroethane according to claim 1.

9. An oxime ether according to claim 1 of the formula

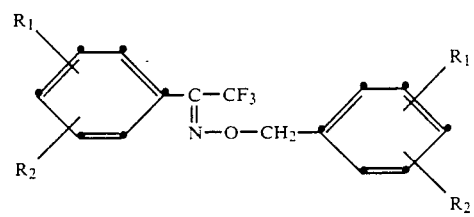

wherein $R_1$ and $R_2$ are as given in claim 1.

10. 1-(4-Fluorophenyl)-1-(4-Fluorobenzyloximino)-2,2,2-trifluoroethane according to claim 1.

11. 1-(3-Trifluoromethylphenyl)-1-benzyloximino-2,2,2-trifluoroethane according to claim 1.

12. An oxime ether according to claim 1 of the formula

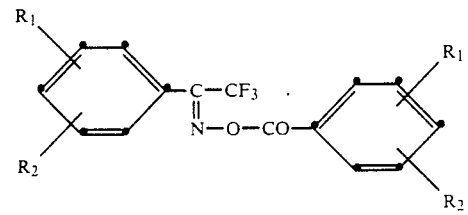

wherein $R_1$ $R_2$ are as defined in claim 1.

13. An oxime ether of the formula

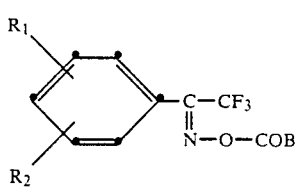

wherein B is a $C_1$-$C_4$alkyl or $C_3$-$C_8$cycloalkyl, $R^1$ is hydrogen, halogen, $C_1$-$C_4$-alkyl, $C_1$-$C_4$-haloalkyl, $C_1$-$C_4$-haloalkoxy or nitro and $R^2$ is hydrogen, halogen, $C_1$-$C_4$-alkyl or $C_1$-$C_4$-alkoxy.

14. An oxime ether of the formula

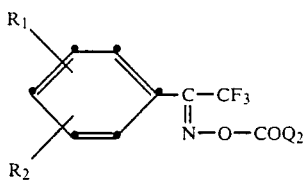

wherein $Q_2$ is a $C_3$-$C_6$alkenyl unsubstituted or substituted by halogen; $R^1$ is hydrogen, halogen, $C_1$-$C_4$-alkyl, $C_1$-$C_4$-haloalkyl, $C_1$-$C_4$-alkoxy, $C_1$-$C_4$-haloalkoxy, or nitro and $R^2$ is hydrogen, halogen, $C_1$-$C_4$-alkyl or $C_1$-$C_4$-alkoxy.

15. 1-Phenyl-1-(1,2,2-trichloroacryloximino)-2,2,2-trifluoroethane according to claim 1.

* * * * *